(12) United States Patent
Herve et al.

(10) Patent No.: US 8,193,518 B2
(45) Date of Patent: Jun. 5, 2012

(54) DEVICE AND METHOD FOR SPATIAL RECONSTRUCTING OF FLUORESCENCE MAPPING

(75) Inventors: Lionel Herve, La Tronche (FR); Jean-Marc Dinten, Lyons (FR); Ludovic Lecordier, Agy (FR)

(73) Assignee: Commissariat à l'énergie atomique et aux énergies alternatives, Paris (FR)

( * ) Notice: Subject to any disclaimer, the term of this patent is extended or adjusted under 35 U.S.C. 154(b) by 52 days.

(21) Appl. No.: 12/889,030

(22) Filed: Sep. 23, 2010

(65) Prior Publication Data
US 2011/0068280 A1    Mar. 24, 2011

(30) Foreign Application Priority Data
Sep. 24, 2009   (FR) ...................................... 09 56610

(51) Int. Cl.
*G01J 1/58* (2006.01)
(52) U.S. Cl. ................................ 250/459.1; 250/458.1
(58) Field of Classification Search ............... 250/458.1, 250/459.1
See application file for complete search history.

(56) References Cited

U.S. PATENT DOCUMENTS

| 6,058,324 | A | 5/2000 | Chance |
|---|---|---|---|
| 6,138,046 | A | 10/2000 | Dalton |
| 6,304,771 | B1 | 10/2001 | Yodh et al. |
| 6,825,930 | B2 | 11/2004 | Cronin et al. |
| 7,321,791 | B2 | 1/2008 | Levenson et al. |
| 7,477,931 | B2 | 1/2009 | Hoyt |
| 7,675,044 | B2 | 3/2010 | Laidevant et al. |
| 2002/0072677 | A1 | 6/2002 | Sevick-Muraca et al. |
| 2005/0065440 | A1 | 3/2005 | Levenson |
| 2005/0264805 | A1 | 12/2005 | Cromwell et al. |
| 2006/0149479 | A1 | 7/2006 | Ma |
| 2008/0051665 | A1 | 2/2008 | Xu et al. |
| 2008/0200780 | A1 | 8/2008 | Schenkman et al. |
| 2008/0260647 | A1 | 10/2008 | Intes et al. |
| 2009/0016921 | A1 | 1/2009 | Fujimoto et al. |
| 2009/0065710 | A1 | 3/2009 | Hunziker et al. |
| 2009/0141959 | A1 | 6/2009 | Can et al. |
| 2009/0153850 | A1 | 6/2009 | Nielsen et al. |
| 2009/0245611 | A1 | 10/2009 | Can et al. |

FOREIGN PATENT DOCUMENTS

| EP | 1 884 765 A1 | 2/2008 |
|---|---|---|
| EP | 2 063 257 A2 | 5/2009 |
| GB | 2 231 958 A | 11/1990 |
| WO | WO 96/20638 A1 | 7/1996 |

(Continued)

OTHER PUBLICATIONS

French Search Report issued on May 10, 2010 in corresponding French Application No. 0956610.

(Continued)

*Primary Examiner* — Mark R Gaworecki
(74) *Attorney, Agent, or Firm* — Oblon, Spivak, McClelland, Maier & Neustadt, L.L.P.

(57) ABSTRACT

The invention concerns a method for locating at least one fluorophore or at least one absorber in a diffusing medium, using at least one excitation radiation and at least one fluorescence detector ($\Phi_{fluo}$), comprising:
a) for at least one pair (radiation source-detector), at least one excitation by the radiation source, and at least one detection of the fluorescence signal emitted by the fluorophore after this excitation,
b) identification of meshing of the volume into mesh elements,
c) estimation of the location of the fluorophore or absorber in its diffusing medium, by computing a function ($P_m$) of at least one of three parameters.

20 Claims, 16 Drawing Sheets

FOREIGN PATENT DOCUMENTS

| WO | WO 96/26431 A1 | 8/1996 |
|---|---|---|
| WO | WO 01/09605 A1 | 2/2001 |
| WO | WO 01/50955 A1 | 7/2001 |
| WO | WO 2005/040769 A2 | 5/2005 |
| WO | WO 2006/032151 A1 | 3/2006 |
| WO | WO 2006/087437 A2 | 8/2006 |
| WO | WO 2006/135769 A1 | 12/2006 |
| WO | WO 2008/132522 A1 | 11/2008 |

OTHER PUBLICATIONS

Huiyuan He et al., "An Analytic, Reflection Method for Time-Domain Florescence Diffuse Optical Tomography Based on a Generalized Pulse Spectrum Technique", Progress in Biomedical Optics and Imaging, Proceedings of SPIE—Multimodal Biomedical Imaging III 2008 SPIE US LNKD, 2008, vol. 6850, No. 68500M, XP 002579460, 68500M-1-68500M-8.

Laurent Guyon et al., "Time-Resolved Fluorescence Tomography in Cancer Research: Backward Versus Toward Geometry", Proceedings of the SPIE—The International Society for Optical Engineering SPIE—The International Society for Optical Engineering USA LNKD, Feb. 12, 2009, vol. 7174, XP 002579495, 11 Pages.

S. R. Arridge, "Optical Tomography in Medical Imaging", Inverse Problems, Apr. 1999, vol. 15 (2), pp. R41-R93.

Qizhi Zhang et al., "Three-Dimensional Diffuse Optical Tomography of Simulated Hand Joints with a 64×64-Channel Photodiodes-Based Optical System", Journal of Optics A., Pure and Applied Optics, 2005, vol. 7, No. 5, pp. 224-231.

A. Cichocki et al., "Multilayer Nonnegative Matrix Factorisation", Electronics Letters, Aug. 3, 2006, vol. 42, No. 16, 2 Pages.

Michael S. Patterson et al., "Time Resolved Reflectance and Transmittance for the Non-Invasive measurement of Tissue Optical Properties", Applied Optics, Jun. 15, 1989, vol. 28, No. 12, pp. 2331-2336.

Jun Wu et al., "Fluorescence Tomographic Imaging in Turbid Media Using Early-Arriving Photons and Laplace Transforms", Proc. Natl. Acad. Sci., Medical Sciences, Aug. 1997, vol. 94, pp. 8783-8788.

Aurélie Laidevant et al., "Experimental Study of Time-Resolved Measurements on Turbid Media: Determination of Optical Properties and Fluorescent Inclusions Characterization", European Conference on Biomedical Optics, 2005, vol. 5859, pp. 58591F-1-58591F-9.

Jean-Marc Dinten et al., "Performance of Different Reflectance and Diffuse Optical Imaging Tomographic Approaches in Fluorescence Molecular Imaging of Small Animals", Medical Imaging 2006: Physics of Medical Imaging, Proceedings of SPIE, 2006, vol. 6142, No. 614215, pp. 614215-1-614215-10.

Anand T. N. Kumar et al., "Fluorescence-Lifetime-Based Tomography for Turbid Media", Optics Letters, Dec. 15, 2005, vol. 30, No. 24, pp. 3347-3349.

S. Lam et al., "Time Domain Fluorescent Diffuse Optical Tomography: Analytical Expressions", Optics Express, Apr. 4, 2005, vol. 13, No. 7, 2263-2275.

Fen Gao, et al., "Time-Domain Fluorescence Molecular Tomography Based on Generalized Pulse Spectrum Technique", Proceedings Biomed, 2006, 3 Pages.

Jeffrey C. Lagarias et al., "Convergence Properties of the Nelder-Mead Simplex Method in Low Dimensions", Society for Industrial and Applied Mathematics Journal on Optimization, 1998, vol. 9, No. 1, pp. 112-147.

S. R. Arridge et al., "The Theoretical Basis for the Determination of Optical Pathlengths in Tissue: Temporal and Frequency Analysis", Phys. Med. Biol., 1992, vol. 37, No. 7, pp. 1531-1560.

R. Cubeddu et al., "Imaging of Optical Inhomogeneities in Highly Diffusive Media: Discrimination between Scattering and Absorption Contributions", Appl. Phys. Letter, Dec. 30, 1996, vol. 69 (27), pp. 4162-4164.

Christoph Bremer et al., "Optical-Based Molecular Imaging: Contrast Agents and Potential Medical Applications", Eur Radiol, 2003, vol. 13, pp. 231-243.

Anuradha Godavarty et al., "Three-Dimensional Fluorescence Lifetime Tomography", Med. Phys., Apr. 2005, vol. 32 (4), pp. 992-1000.

Amir H. Gandjbakhche et al., "Effects of Multiple-Passage Probabilities on Fluorescent Signals from Biological Media", Applied Optics, Jul. 1, 1997, vol. 36, No. 19, pp. 4613-4619.

David Hall et al., "Simple Time-Domain Optical Method for Estimating the Depth and Concentration of a Fluorescent Inclusion in a Turbid Medium", Optics Letters, Oct. 1, 2004, vol. 29, No. 19, pp. 2258-2260.

Aurélie Laidevant et al., "Effects of the Surface Boundary on the Determination of the Optical Properties of a Turbid Medium with Time-Resolved Reflectance", Applied Optics, Jul. 1, 2006, vol. 45, No. 19, pp. 4756-4764.

Aurélie Laidevant et al., "Analytical Method for Localizing a Fluorescent Inclusion in a Turbid Medium", Applied Optics, Apr. 10, 2007 vol. 46, No. 11, pp. 2131-2137.

Adam Liebert et al., "Evaluation of Optical Properties of Highly Scattering Media by Moments of Distributions of Times of Flight of Photons", Applied Optics, Oct. 1, 2003, vol. 42, No. 28, pp. 5785-5792.

Maureen A. O'Leary, "Imaging with Diffuse Photon Density Waves", A Dissertation in Physics, Faculties of the University of Pennsylvania, 1996, pp. 1-192 plus cover pages.

Vasilis Ntziachristos et al., "Experimental Three-Dimensional Fluorescence Reconstruction of Diffuse Media by Use of a Normalized Born Approximation", Optics Letters, Jun. 15, 2001, vol. 26, No. 12, pp. 893-895.

Eva M. Sevick-Muraca et al., Origin of Phosphorescence Signals Reemitted from Tissues, Optics Letters, Dec. 1, 1994, vol. 19, No. 23, pp. 1928-1930.

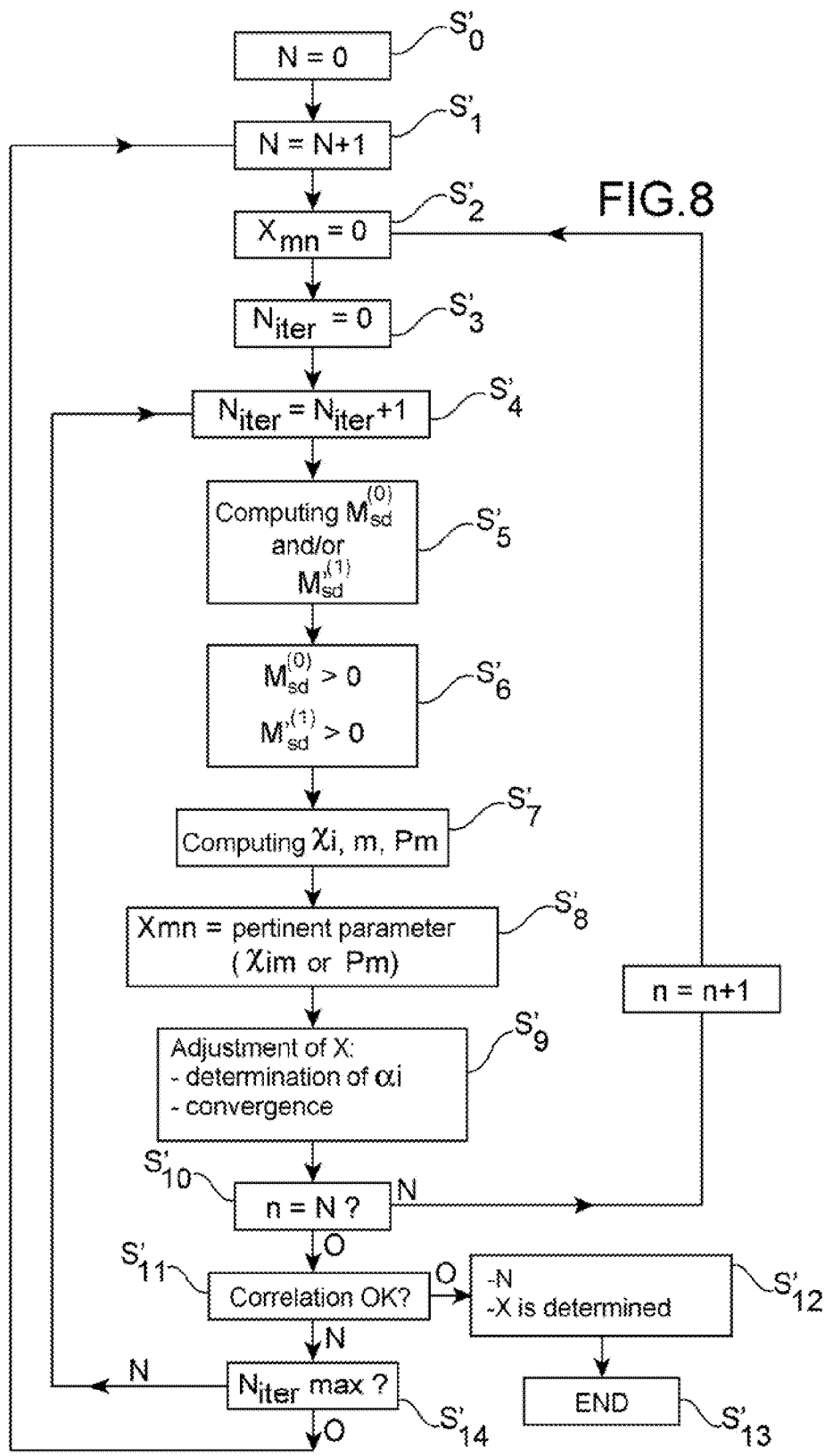

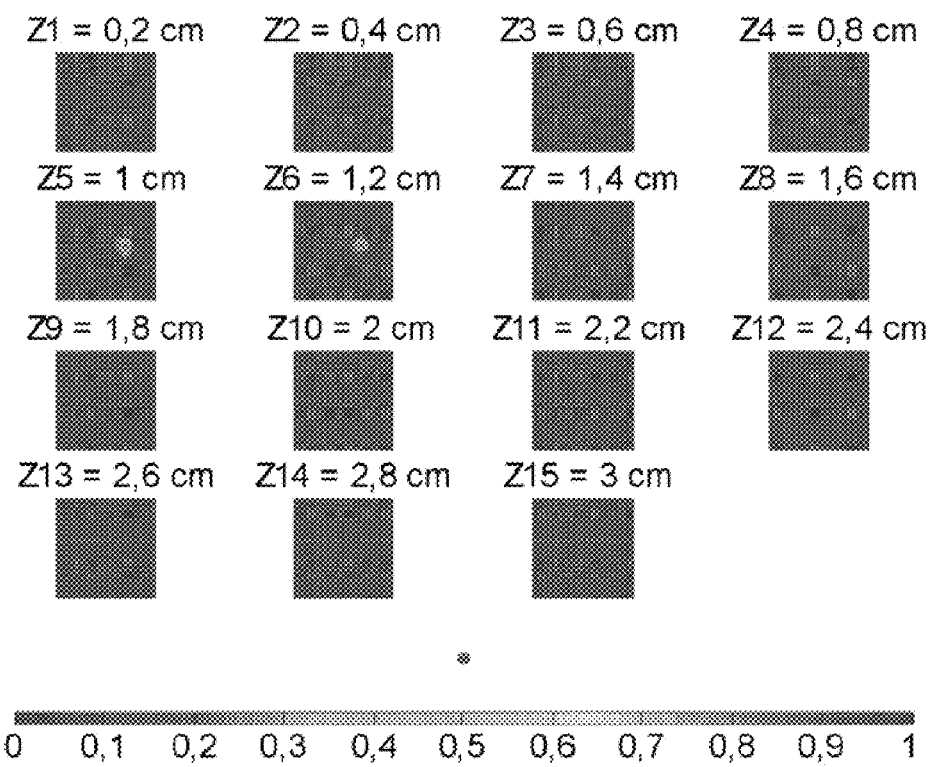
FIG.11C
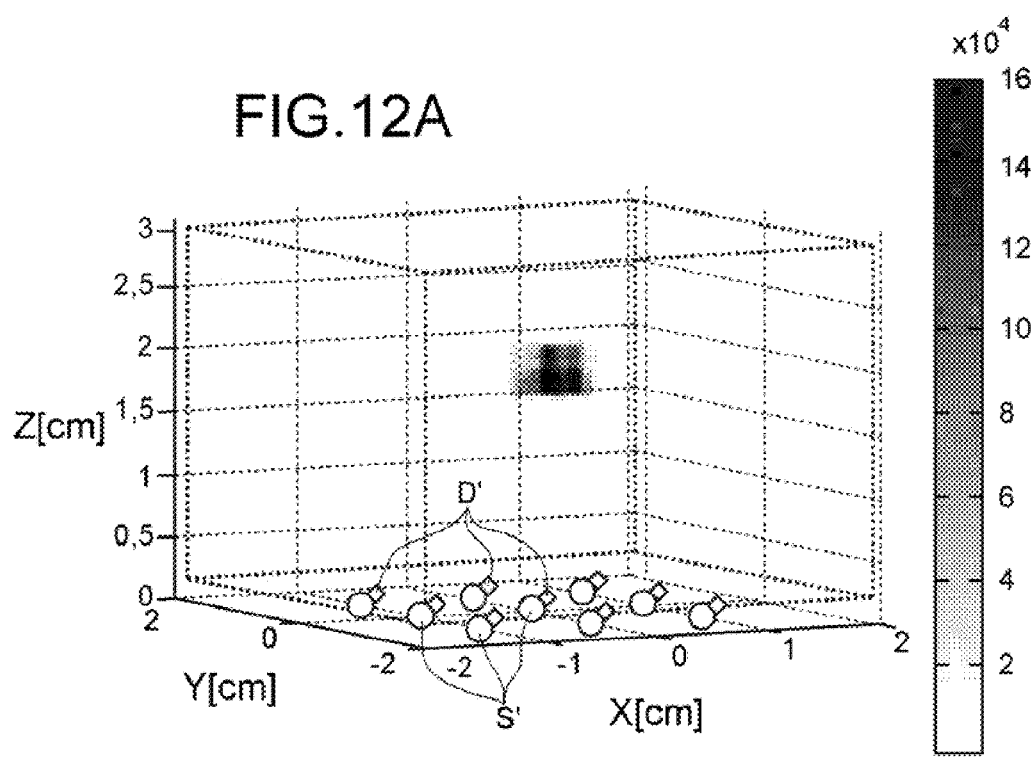

DEVICE AND METHOD FOR SPATIAL RECONSTRUCTING OF FLUORESCENCE MAPPING

TECHNICAL FIELD AND PRIOR ART

The invention concerns the field of fluorescence molecular imaging of biological tissues using time-resolved optical methods.

It applies in particular to optical molecular imaging of small animals and to optical molecular imaging in man (brain, breast, other organs in which fluorophores can be injected).

The application that is notably targeted is the detection of prostate cancer.

At the current time, the locating of diseased cells can be made using biopsy techniques.

However, to find the position, even approximate position, of these cells, several samples must be taken. This invasive technique is evidently difficult to implement and is time-consuming.

The problem therefore arises of determining the location, even approximate location, of fluorophores attached to a region of a medium e.g. a biological medium.

In some cases, it is even sought to locate fluorophores with a view to subsequent surgical intervention.

Optical techniques for fluorescence molecular imaging are therefore being increasingly developed at the present time through the use of specific fluorescent markers. These preferably attach themselves to the target cells of interest (e.g. cancer cells) and offer better detection contrast than non-specific markers. The objective of these techniques is to locate fluorescence spatially but also to determine the concentration thereof.

Optical tomography systems use various light sources. Existing apparatus operates in continuous mode or in frequency-mode (which uses frequency-modulated lasers) and finally in temporal mode which uses pulsed light sources, such as pulsed lasers.

Temporal data are obtained when a pulsed source is used delivering a short signal at a determined rate. In this case, the term time-resolved diffuse imaging is used. Temporal data are data which contain the most informational content on the imaged tissue, but for which reconstruction techniques are the most complex. The measurement at each acquisition point is effectively a time-dependent function called TPSF for Temporal Spread Function.

It is sought to extract simple parameters from the TPSF, whose theoretical expression is known. Resolution of the inverse problem then allows the distribution of fluorescence to be found.

Locating techniques are known from document EP 1 884 765 for example.

However, these techniques do not give satisfaction notably in so-called "back-diffusion" geometry in which sources and detectors lie on one same side of the object or of the medium being examined.

DISCLOSURE OF THE INVENTION

The inventors have found, when applying known techniques for time-resolved diffuse optical imaging, that a certain number of problems arise. Different distributions of fluorophores may effectively lead to the same measurements, a measurement being the intensity of fluorescence for example or the mean time-of-flight, notably in reflection geometry.

For any medium, knowing its optical properties, it is possible to compute photon density for a Dirac point source located at $r_s$ and at $t=0$ s, using Green functions.

These functions $G_s(r,t)$ can be determined using a Monte-Carlo simulation, or by solving the radiation transfer equation, or most often, by solving the diffusion equation (1) to which boundary conditions are added:

$$\frac{\partial G_s(r, t)}{c\partial t} - \nabla D \nabla G_s(r, t) + \mu_a G_s(r, t) = \delta(r - r_s, t) \tag{1}$$

The Gs moments, i.e. the quantities:

$$G_s^{(n)}(r) = M^n(G_s) = \int_0^\infty Gs(r, t) t^n dt \tag{1'}$$

follow the differential equations given by (2):

$$-\nabla D \nabla G_s^{(n)}(r) + \mu_a G_s^{(n)}(r) = \delta(r - r_s, n) + \frac{n}{c} G_s^{(n-1)} \tag{2}$$

Therefore, $G_s^{(0)}$ is the solution of the differential equation (2) with only the Dirac as source term, and $G_s^{(n)}$ is the solution when the source term is proportional to $G_s^{(n-1)}$. The sequence of $G_s^{(n)}$ functions is therefore found by successive steps.

For an infinite homogeneous medium, an analytical solution of (1) is known. This is:

$$G_s^\infty(r, t) = \frac{c}{(4\pi Dct)^{\frac{3}{2}}} \exp\left(-\frac{r^2}{4Dct} - \mu_a ct\right) \tag{3}$$

The moments of this function are also determined analytically;
The 2 first are:

$$G_s^{(0)}(r) = \exp(-k \cdot |r-r_s|)/(|r-r_s|D) \tag{4}$$

$$G_s^{(1)}(r) = \exp(-k \cdot |r-r_s|)/(2c\sqrt{\mu_a D}) \tag{5}$$

These formulas are of interest when simulating measurements for which it is possible to insert the sources (and detectors) in the medium (for example by means of optical fibres at the tip of a biopsy needle).

In the remainder of this application, some embodiments have recourse to moments 0 and 1 of the measurement $M_{sd}(t)$ prompted by the source s and measured by the detector d.

They are useful since they give the total detected energy $I_{sd}$ and the time-of-flight $T_{sd}$.
Indeed:

$$I_{sd} \int_0^\infty M_{sd}(t) \cdot t^0 dt = M_{sd}^{(0)} \tag{6}$$

and $$T_{sd} = \frac{\int_0^\infty M_{sd}(t) \cdot t^1 \cdot dt}{\int_0^\infty M_{sd}(t) \cdot t^0 \cdot dt} = M_{sd}^{(1)}/M_{sd}^{(0)} \tag{7}$$

The description of the chain of physical processes is the following; each photon is:
- emitted by the source as per a probability density described by the time response of the source,
- and then propagates, following the probability described by the function $G_s(r,t)$, as far as a point r of the mesh,
- it is then absorbed according to the concentration and effective cross-section of the fluorophore at r,
- and then emitted by the fluorophore at the fluorescence wavelength at r,
- it then propagates as far as the detector d as per a probability $G_d(r,t)$
- and it is finally detected by the detector, which has a time response.

Owing to the inverse return properties of light, $G_d(r,t)$ is the solution of (1) by replacing $r_s$ by $r_d$ ($r_d$ being the position of the detector under consideration).

As a result, for a "Dirac" fluorophore arranged at r, the measurement $M_{sd}$ performed by the detector d for a medium illuminated by the source s is written:

$$M_{sd}(t)=S(t)*G_s(r,t)*F(r,t)*G_d(r,t)*D(t) \quad (8)$$

The sign * represents temporal convolution, F(t) is the time response of the fluorophore, S(t) is the temporal function of the source and D(t) is the time response of the detector.

In practice, one is capable of determining the source signal detected by the detector, making it possible to arrive at a convolution of the respective time responses of the source and detector. In other words, it is not necessary to estimate the time response of the source and the time response of the detector separately i.e. the convolution S(t)*D(t).

Here, we have assumed that the temporal functions of the sources and detectors are independent of their position; however, if this were not the case, this problem could easily be treated by writing $S_s$ and $D_d$, the indices s and d being the indices of the different sources and different detectors.

For an assembly of fluorophores in volume $\chi$, we obtain:

$$M_{sd}(t) = \int\int_\Omega\int S(t)*G_s(r,t)*F(r,t)*G_d(r,t)*D(t)dr \quad (9)$$

Owing to the computing properties of moments on the products of convolutions, for the first two moments of Msd(t) we obtain:

$$M_{sd}^{(0)}(t) = \int\int_\Omega\int S^{(0)} \cdot G_s^{(0)}(r) \cdot F^{(0)}(r) \cdot G_d^{(0)}(r) \cdot D^{(0)} dr \quad (10)$$

$$M_{sd}^{(1)} = \int\int_\Omega\int dr \begin{cases} S^{(1)} \cdot G_s^{(0)}(r) \cdot F^{(0)}(r) \cdot G_d^{(0)}(r) \cdot D^{(0)} + \\ S^{(0)} \cdot G_s^{(1)}(r) \cdot F^{(0)}(r) \cdot G_d^{(0)}(r) \cdot D^{(0)} + \\ S^{(0)} \cdot G_s^{(0)}(r) \cdot F^{(1)}(r) \cdot G_d^{(0)}(r) \cdot D^{(0)} + \\ S^{(0)} \cdot G_s^{(0)}(r) \cdot F^{(0)}(r) \cdot G_d^{(1)}(r) \cdot D^{(0)} + \\ S^{(0)} \cdot G_s^{(0)}(r) \cdot F^{(0)}(r) \cdot G_d^{(0)}(r) \cdot D^{(1)} \end{cases} \quad (11)$$

Taking inspiration from (7) we obtain:

$$M_{sd}^{(1)} = \int\int_\Omega\int dr \cdot S^{(0)} \cdot G_s^{(0)}(r) \cdot F^{(0)}(r) \cdot \quad (12)$$
$$G_d^{(0)}(r) \cdot D^{(0)}(T_s + T_s(r) + T(r) + T_d(r) + T_d)$$

In this formula:
- $T_s$ is the mean time of the source function,
- $T_s(r)$ is the mean time-of-flight between s and r,
- $T(r)$ is the lifetime $\tau$ of the fluorophore, assumed to be invariant as per position,
- $T_d(r)$ is the mean time-of-flight between r and the detector d,
- $T_d$ is the mean response time of the detector.

In infinite, homogeneous cases, according to formulas (4) and (5) it is seen that Ts(r), the mean time-of-flight between s and r, is just equal to:

$$|r-r_s|/(2c\sqrt{\mu_a D}).$$

Therefore, $v=2c\sqrt{\mu_a D}$ can be interpreted as the mean velocity of the photons in this medium.

With regard to the prostate, typically v=5 cm/ns is obtained. The same applies to Td(r).

If the fluorophore is a single, point fluorophore, the formulas (10) and (12) become simpler.

If the fluorophore lies at position $r_0$, the formulas become:

$$I_{sd}=M_{sd}^{(0)}=S^{(0)} \cdot G_s^{(0)}(r_0) \cdot F^{(0)}(r_0) \cdot G_d^{(0)}(r_0) \cdot D^{(0)} \quad (13)$$

and $$T_{sd} = \frac{M_{sd}^{(1)}}{M_{sd}^{(0)}} = T_s + T_s(r_0) + \tau + T_d(r_0) + T_d \quad (14)$$

$S^{(0)}D^{(0)}$ and Ts+Td can be measured during a calibration operation, during which the source is placed facing the detector. This gives a calibration signal whose zero-order moment is equal to $S^{(0)}D^{(0)}$ and the first-order normalized moment equals to Ts+Td Therefore, the measured time-of-flight is equal to the mean lag of the source to which are added the time-of-flight between the source and the fluorophore, the lifetime of the fluorophore, the time-of-flight between the fluorophore and the detector and the response time of the detector.

Let us now move on to the problem of fluorescence reconstruction, first with regard to an assembly of fluorophores. It is ascertained, in back-diffusion, that the reconstruction of fluorescence maps in a diffuse medium is very difficult.

The inventors have found, notably in reflection geometry, that different configurations lead to identical measurements. For example, a fluorophore that is broadly distributed can produce a measurement equivalent to a point fluorophore. It therefore appears that during the reconstruction of fluorophores in reflection, there is a strong need for prior hypotheses. One type of hypothesis that can be used is to state that the fluorophores are point fluorophores located at given sites. Said hypothesis can be called a supporting constraint hypothesis.

One first solution is to consider that the fluorophore is single and located as a point in the medium being examined.

Another solution is to consider a plurality of point fluorophores distributed in the examined medium.

The above formula (14) can be used to reconstruct fluorescence by "triangulation", for example using the technique described in document EP 1 884 765.

In particular, when the medium is homogeneous infinite:

$$T_{sd}-T_s-\tau-T_d=(|r-r_s|+|r-r_d|)/(2c\sqrt{\mu_a D}).$$

Therefore, by combining several source-detector pairs, it is possible to proceed back to position r. The disadvantage of this method is that it provides as many solutions as there are source-detector pairs.

For this purpose, the invention proposes a method to locate at least one fluorophore, in a diffusing medium, using at least one pulsed radiation source capable of emitting radiation to excite this fluorophore and at least one detector capable of measuring a fluorescence signal emitted by this fluorophore, which comprises:

illuminating the medium by a radiation source, detecting, by at least one detector, the signal produced by the medium at the fluorescence wavelength, for at least one source-detector pair, performing temporal distribution $M_{sd}(t)$ of the signal received by the detector, the diffusing medium being discretized into M voxels, characterized in that the method also comprises the computing of at least one basic parameter $\chi^N_{i,m}$, which, for at least one of said temporal distributions $M_{sd}(t)$, combines at least one magnitude obtained from at least one moment of said distribution, with at least one estimation of this magnitude, this estimation being made by considering that there are N fluorophores, each then occupying a voxel of the medium as per a distribution m.

Said method may also comprise the determination of a combined parameter $P^N_m$, combining at least one or two basic parameters $\chi^N_{i,m}$.

At least one of the basic parameters may be:

a first basic parameter $\chi^N_{1,m}$, which is the sum, for all pairs (source, detector), of the differences between the value of the measured intensity $M_{sd}^0$ for each source-detector pair, and an estimation of zero-order moment for each source-detector pair obtained using Green functions $G_{smn}$ and $G_{mnd}$, for the source and detector of each pair, this estimation being made by considering that the N fluorophores are distributed in the voxels of the medium as per configuration m in which the fluorophores are distributed in the voxels $m_n$;

or a second basic parameter $\chi^N_{2,m}$, which is the sum, for all source-detector pairs, of the differences for each source-detector pair between the mean measured source-detector time-of-flight (first-order normalized moment of M(t)) corrected by known temporal magnitudes relating to the source, to the detector and to the fluorophore, and the estimation of this corrected time-of-flight, this estimation being made by considering that the N fluorophores are distributed in the voxels of the medium as per configuration m.

For example, the basic coefficient $\chi_{1m}^N$ can be such that:

$$\chi^N_{1m} = \min_{\alpha_1,...\alpha_N} \sum_{sd} \frac{(M_{sd}^{(0)} - M_{sd,m}^{theo0}(\alpha_1,...\alpha_N))^2}{\sigma^2(M_{sd}^0)}$$

where:

$$M_{sd,m}^{theo0}(\alpha_1,...\alpha_N) = \sum_{n=1}^{N} \alpha_n G_{sm_n} G_{m_n d}$$

a configuration m corresponding to N fluorophores distributed in the voxels $m_n$, $1 \leq n \leq N$, $G_{smn}$ (respectively $G_{mnd}$) representing the energy transfer functions between the source and the voxel $m_n$ (respectively the voxel $m_n$ and detector d). The coefficients $\alpha_n$, which can be considered as intensities, are obtained by the minimization operation, as is $\chi_{1m}$;

each element $(M_{sd}^0 - M_{sd,m}^{theo0}(\alpha_1,...\alpha_N))$ of the sum then representing the difference between:

the value of the measured intensity $M_{sd}^0$ for the selected source-detector pair, and an estimation of the zero-order moment $M_{sd}^0$, obtaining using firstly the Green functions $G_{smn}$ and $G_{mnd}$, and secondly a set of coefficients $\alpha_n$ each of which is assigned to a fluorophore and which represents the intensity of fluorescence emission by the latter.

The second basic parameter $\chi_{2m}^N$ can be such that:

$$\chi^N_{2m} = \min_{\alpha'_1,...\alpha'_N} \sum_{sd} \frac{((T_{sd} - T_s - \sigma - T_d) - (T_{sd,m}^{theo}(\alpha'_1,...\alpha'_N)))^2}{\sigma^2(T_{sd})}$$

where:

$$T_{sd,m}^{theo}(\alpha'_1,...\alpha'_N) = \frac{\sum_{n=1}^{N} \alpha'_n G_{sm_n} G_{m_n d}(T_{sm_n} + T_{m_n d})}{\sum_{n=1}^{N} \alpha'_n G_{sm_n} G_{m_n d}}$$

Ts, Td and τ respectively representing the response time of the source, of the detector and the duration of fluorescence of the fluorophore, $Tsm_n$ and $Tm_n d$ representing the respective times-of-flight between the source and the fluorophore located in the voxel $m_n$, and between the fluorophore located in voxel $m_n$ and the detector, the coefficient $\sigma^2(Tsd)$ corresponding to an estimation of the variance of distribution Tsd, $T^{theo}_{sd}(\alpha'1...\alpha'N)$ then representing an estimation of the first-order normalized moment of function $M_{sd}(t)$, the coefficients $\alpha'_N$ being obtained with the minimization operation.

With said method, it is also possible to determine a combined parameter $P^N_m$, equal to the sum or to the product of the basic coefficients $\chi^N_{1,m}$ and $\chi^N_{2,m}$, the combined parameters $P^N_m$ of lowest value then corresponding to the fluorophore distributions the closest to the effective fluorophore distribution.

The number of fluorophores can equal 1, each basic parameter $\chi^{N=1}_{1,m}$ and $\chi^{N=1}_{2,m}$ then being determined by considering that the fluorophore is single and is located in voxel m. $\chi^{N=1}_{1,m}$ and $\chi^{N=1}_{2,m}$ can then be determined according to the following equations:

$$\chi_{1m} = \min_{\alpha_m} \sum_{sd} \frac{(M_{sd}^0 - \alpha_m \cdot G_{sm} G_{md})^2}{\sigma^2(M_{sd}^0)}$$

and $$\chi_{2m} = \sum_{s,d} \frac{((T_{sd} - T_s - \tau - T_d) - (T_{sm} + T_{dm}))^2}{\sigma^2(T_{sd})}$$

$M_{sd}^0$ representing the zero-order moment of the function Msd(t),

Gsm and Gmd being energy transfer functions, for each source-detector pair sd, between respectively the source s and the voxel m and between voxel m and the detector d, Tsm and Tdm representing the respective times-of-flight between the source and voxel m, and voxel m and the detector d, Ts, Td and τ respectively representing the response times of the source, of the detector and the duration of fluorescence of the fluorophore, the coefficient $\sigma^2(Tsd)$ corresponding to an estimation of the variance of distribution Tsd.

With this method, it is also possible to determine a combined parameter $P_m^N$, equal to the sum or to the product of the basic coefficients $\chi^{N=1}_{1,m}$, and $\chi^{N=1}_{2,m}$, the combined parameters $P_m^{N=1}$ of lowest value then corresponding to the distributions of the fluorophores the closest to the effective distribution of the fluorophores.

The invention also proposes a method to locate at least one fluorophore or at least one absorber in a diffusing medium, using at least one pulsed radiation source capable of emitting radiation to excite this fluorophore or this molecule, and at least one detector capable of measuring a fluorescence signal ($\Phi_{fluo}$) emitted by this fluorophore or an emission signal emitted by this absorber, comprising:

a) for at least one pair (radiation source, detector), at least one excitation by radiation derived from the radiation source of this pair, and at least one detection by the detector of this pair of fluorescence signal emitted by this fluorophore after this excitation, or of the emission signal emitted by this absorber, b) identification of meshing (M) of the volume into mesh elements (m);

c) an estimation of the location of the fluorophore or of the absorber in its diffusing medium, by computing a function ($\chi_{1m}, \chi'_{1m}, \chi_{2m}, \chi'_{2m}, P_m$) of at least one of the three following parameters, for each element of the mesh:

$\chi_{1m}$ (or $\chi_{1m}^N$) which is the sum, for all source-detector pairs, of the differences between the value of measured intensity $M_{sd}^0$ for each source-detector pair, optionally corrected by estimation of intensity contribution, measured by the detector, of already located fluorophores, and an estimation of the zero-order moment for each source-detector pair obtained using the Green functions Green $G_{sm}$ and $G_{md}$ (or $G_{smn}$ and $G_{mnd}$) for the source and detector of each pair and the mesh element;

$\chi_{2m}$ (or $\chi_{2m}^N$) which is the sum, for all source-detector pairs, of the differences for each source-detector pair between the mean measured source-detector time-of-flight (first-order normalized moment of M(t)), optionally corrected by estimation of the time-of-flight contribution by already located fluorophores, and this same, modelled, first-order normalized moment, $\chi_{3m}$ which is the sum, over all the source-detectors pairs, of the correlations for each source-detector pair between firstly a value of the measured intensity ($I_{sd}$=M(0) (t)) determined by the zero-order moment of M(t) denoted M(0) (t), optionally corrected by estimation of the intensity contribution measured by the detector of already located fluorophores, and secondly a value of this zero-order moment modelled using the product $G_{sm} \cdot G_{dm}$ of the Green functions $G_{sm}$ and $G_{md}$, for the source and detector of each pair and the mesh element.

$\chi_{1m}^N, \chi_{2m}^N, \chi_{3m}$ can have the form already indicated above, or as in the remainder of this application.

Said function of at least one of the three parameters can be a linear function of at least one of said parameters and/or a non-linear function of at least one of said parameters.

Therefore, for example, another parameter is $\chi^N_{4,m}$:

$$\chi^N_{4m} = \min_{\alpha_1,...\alpha_N} \left[ \sum_{sd} \frac{(M_{sd}^{(0)} - M_{sd}^{theo0}(\alpha_1, ... \alpha_N))^2}{\sigma^2(M_{sd}^0)} + \sum_{sd} \frac{((T_{sd} - T_s - \sigma - T_d) - (T_{sd}^{theo}(\alpha_1, ... \alpha_N)))^2}{\sigma^2(T_{sd})} \right]$$

where:

$$M_{sd}^{theo0}(\alpha_1, ... \alpha_N) = \sum_{n=1}^{N} \alpha_n G_{sm_n} G_{m_n d}$$

and:

$$T_{sd}^{theo}(\alpha_1, ... \alpha_N) = \frac{\sum_{n=1}^{N} \alpha_n G_{sm_n} G_{m_n d}(T_{sm_n} + T_{m_n d})}{\sum_{n=1}^{N} \alpha_n G_{sm_n} G_{m_n d}}$$

An operator selects one or more of these parameters and/or one or more functions of these parameters, and computes the same to obtain initial information on the location of at least one fluorophore, optionally after comparing the computed results with one or more threshold values, or one or more minimum values, or one or more maximum values.

Irrespective of the embodiment of the invention, it is additionally possible, for the locating of several fluorophores, to carry out a step to adjust all the intensity contributions of already located fluorophores to the measured intensity.

It is also possible to perform a step to compute a correlation between the measured intensity and all the intensity contributions of all the fluorophores.

If there are several fluorophores of unknown number, the method may further comprise a step ($S'_1$) to increment the number of fluorophores if the computing of a correlation is not satisfactory.

The medium surrounding the fluorophore or the absorber may be of infinite type or semi-infinite type or in slab form limited by two parallel surfaces, or of any shape its outer surface being discretized into a series of planes.

One method according to the invention is particularly well suited to the case in which the sources of radiation and the detectors have reflection geometry.

The invention also concerns a device to locate at least one fluorophore, in a diffusing medium, comprising at least one pulsed radiation source capable of emitting radiation to excite this fluorophore, and at least one detector capable of measuring a fluorescence signal emitted by this fluorophore, comprising:

means, for at least one source-detector pair, to perform temporal distribution $M_{sd}(t)$ of the signal received by the detector, means to produce a mesh (M) of the volume in mesh elements m;

means to compute at least one basic parameter $\chi^N_{i,m}$, which, for at least one of said temporal distributions $M_{sd}(t)$, combines at least one magnitude obtained from at least one moment of said distribution, and at least one estimation of this magnitude, this estimation being made by considering that there are N fluorophores, each then occupying a voxel of the medium as per a distribution m.

The basic coefficient $\chi_{1m}^N$ can be such that:

$$\chi_{1m}^N = \min_{\alpha_1,...\alpha_N} \sum_{sd} \frac{(M_{sd}^{(0)} - M_{sd,m}^{theo0}(\alpha_1, ... \alpha_N))^2}{\sigma^2(M_{sd}^0)}$$

-continued where:

$$M_{sd,m}^{theo0}(\alpha_1, \ldots \alpha_N) = \sum_{n=1}^{N} \alpha_n G_{sm_n} G_{m_n d}$$

a configuration m corresponding to N fluorophores distributed in the voxels $m_n$, $1 \leq n \leq N$, $G_{smn}$ (respectively $G_{mnd}$) representing the energy transfer functions between the source and the voxel $m_n$ (respectively the voxel $m_n$ and the detector d). The coefficients $\alpha_n$, which can be considered as intensities, are obtained with the minimization operation, as is $\chi_{1m}$;

Each element $(M_{sd}^0 - M_{sd,m}^{theo0}(\alpha_1, \ldots \alpha_N))$ of the sum then representing the difference between:

the value of the measured intensity $M_{sd}^0$ for the selected source-detector pair, and an estimation of the zero-order moment $M_{sd}^0$, obtained using firstly the Green functions $G_{smn}$ and $G_{mnd}$, and secondly a set of coefficients $\alpha_n$ of which each one is assigned to a fluorophore and represents the intensity of the fluorescence emission thereof.

And the second basic parameter $\chi_{2m}^N$ can be such that:

$$\chi_{2m}^N = \min_{\alpha'_1, \ldots \alpha'_N} \sum_{sd} \frac{((T_{sd} - T_s - \sigma - T_d) - (T_{sd,m}^{theo}(\alpha'_1, \ldots \alpha'_N)))^2}{\sigma^2(T_{sd})}$$

where:

$$T_{sd,m}^{theo}(\alpha'_1, \ldots \alpha'_N) = \frac{\sum_{n=1}^{N} \alpha'_n G_{sm_n} G_{m_n d}(T_{sm_n} + T_{m_n d})}{\sum_{n=1}^{N} \alpha'_n G_{sm_n} G_{m_n d}}$$

Ts, Td and τ respectively represent the response time of the source, of the detector and the duration of fluorescence of the fluorophore, $Tsm_n$ and $Tm_n d$ representing the respective times-of-flight between the source and the fluorophore located in the voxel $m_n$, and between the fluorophore located in voxel $m_n$ and the detector, the coefficient $\sigma^2(Tsd)$ corresponding to an estimation of the variance of distribution Tsd, $T^{theo}_{sd,m}(\alpha'1 \ldots \alpha'N)$ then representing an estimation of the first-order normalized moment of function $M_{sd}(t)$, the coefficients $\alpha'_N$ being obtained with the minimization operation.

Said device may comprise means to determine a combined parameter $P_m^N$, equal to the sum or to the product of the basic coefficients $\chi^N_{1,m}$ and $\chi^N_{2,m}$.

If the number of fluorophores is equal to 1, each basic parameter $\chi^{N=1}_{1,m}$ and $\chi^{N=1}_{2,m}$ can be determined by considering that the fluorophore is single and located in voxel m.

$\chi^{N=1}1,m$ and $\chi^{N=1}_{2,m}$ can be determined according to the following equations:

$$\chi_{1m} = \min_{\alpha_m} \sum_{sd} \frac{(M_{sd}^0 - \alpha_m \cdot G_{sm} G_{md})^2}{\sigma^2(M_{sd}^0)}$$

and $$\chi_{2m} = \sum_{s,d} \frac{((T_{sd} - T_s - \tau - T_d) - (T_{sm} + T_{dm}))^2}{\sigma^2(T_{sd})}$$

$M_{sd}^0$ representing the zero-order moment of the function Msd(t),

Gsm and Gmd being energy transfer functions, for each source-detector pair sd, between the source s and voxel m and between voxel m and detector d respectively, Tsm and Tdm representing the respective times-of-flight between the source and voxel m, and voxel m and the detector d, Ts, Td and τ respectively representing the response times of the source, of the detector and the duration of fluorescence of the fluorophore, the coefficient $\sigma^2(Tsd)$ corresponding to an estimation of the variance of distribution Tsd.

The invention also concerns a device to locate at least one fluorophore or at least one absorber in a diffusing medium, comprising at least one radiation source capable of emitting radiation to excite this fluorophore or this molecule, and at least one detector capable of measuring a fluorescence signal ($\Phi_{fluo}$) emitted by this fluorophore or an emission signal emitted by this absorber, comprising:

a) means for producing a mesh (M) of the volume in mesh elements m;

b) means to estimate the location of the fluorophore or of the absorber in its diffusing medium, by computing a function ($P_m$) of at least one of the three following parameters:

$\chi_{1m}$ (or $\chi_{1m}^N$) which is the sum over all source-detector pairs, of the differences between the value of the measured intensity $M_{sd}^0$ for each selected source-detector pair, optionally corrected by the estimation of the contribution to the intensity made by already located fluorophores, and an estimation of the zero-order moment obtained using the Green functions $G_{sm}$ and $G_{md}$ (or $G_{smn}$ and $G_{mnd}$), $\chi_{2m}$ (or $\chi_{2m}^N$) which is the sum over all source-detector pairs of the differences, for at least one measurement, between the mean measured source-detector time-of-flight (first-order normalized moment of M(t)), optionally corrected by the estimation of the contribution of already located fluorophores to the time-of-flight, and this same modelled, first-order normalized moment, $\chi_{3m}$ which is the sum over all source-detector pairs of the correlations between firstly a value of the measured intensity ($I_{sd}$=M(0)(t)) determined by the zero-order moment of M(t), denoted M(0)(t), optionally corrected by the estimation the contribution, to the intensity, by already located fluorophores, and secondly a value of this modelled zero-order moment (the product $G_{sm} \cdot G_{dm}$).

Said function of at least one of the three parameters can be a linear function of at least one of said parameters and/or a non-linear function of at least one of said parameters.

Whatever its embodiment, said device may comprise means, if there are a plurality of fluorophores, to perform a step to adjust all intensity contributions by already located fluorophores to the measured intensity.

It may additionally comprise means to compute a correlation between the measured intensity and all the intensity contributions by all the fluorophores.

Means can be provided to increment the number of fluorophores if the computing of a correlation is not satisfactory.

In said device, the sources of radiation and the detectors preferably have reflection geometry.

BRIEF DESCRIPTION OF THE DRAWINGS

FIGS. 7 and 8 are examples of a method according to the invention.

FIGS. 11A-11C and 12A-12C illustrate the results obtained with a method according to the invention.

DETAILED DESCRIPTION OF EMBODIMENTS OF THE INVENTION

Figure 1A:
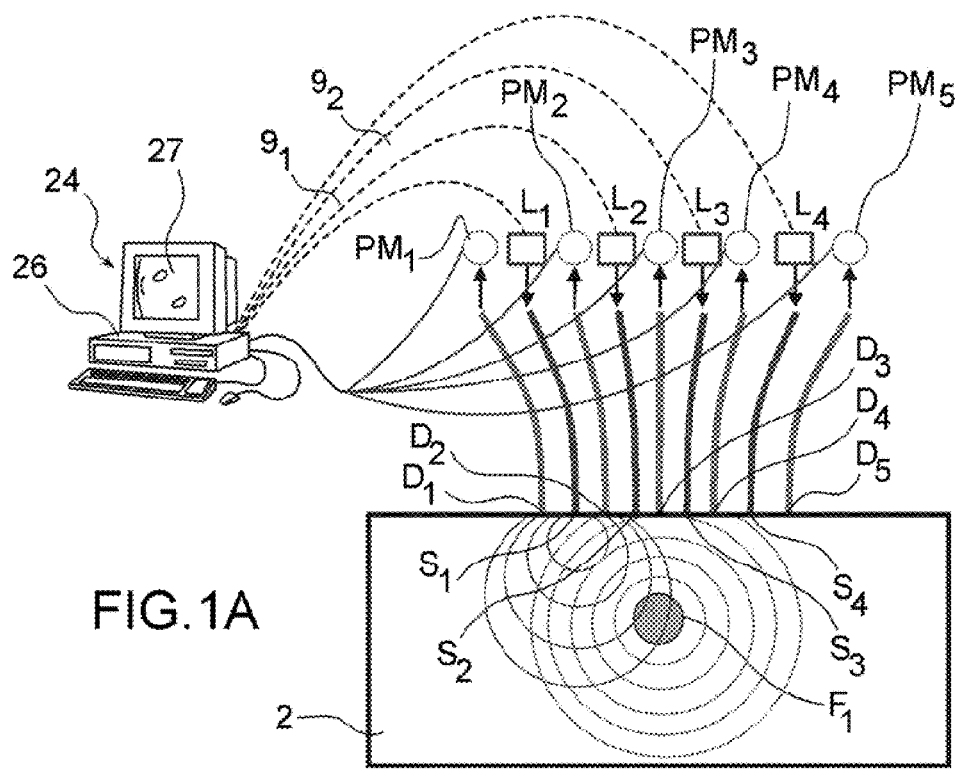
FIGS. 1A-1B schematically illustrate an experimental configuration of fluorescence tomography in reflection geometry, which can be implemented under the invention.

An experimental device in reflection geometry (in which the sources and detectors lie on the same face of the object or of the examined medium) is illustrated in FIG. 1A.

The radiation source and the detection means respectively may be the tip of an optical fibre conveying excitation light into the medium and the tip of an optical fibre which collects part of the emission light.

The diffusing medium 2 can be seen in the figure, containing fluorescent inclusions $F_i$ (here one inclusion $F_1$ is shown) and a set of sources $S_i$ (here each of the sources e.g. a laser source $L_i$, is connected to a fibre, therefore the source can be considered to be the tip of the fibre closest to the medium 2) sequentially bringing the light into the medium.

A set of detection points is designated $D_i$: here each of the detectors $PM_i$ is connected to a fibre, therefore the detector can be considered to be the tip of the fibre closest to the medium 2. These detectors are used to sample the density of fluorescence photons.

In general, the number $n_s$ of sources can be any number. For example, there may be only one source, or 2 or 3, or any number $n_s>3$.

The number $n_d$ of detectors can be any number. For example, there may be a single detector, or 2 or 3 or any number $n_d>3$.

Preferably $n_s>2$ or $>3$ or $>5$ and $n_d>2$ or $>3$ or $>5$.

In applications in which great compactness is required, in endoscopy for example, the number $n_s$ of sources can lie between 1 and 10.

Each source $L_i$ can be a pulsed laser source or an optical fibre connected to a remote pulsed laser (which is the case for the configuration in FIG. 1A). It is also possible to have a single source connected to several fibres (configuration in FIG. 1B in which there is a single laser source L, the other aspects of the system being the same as those in FIG. 1A), and means e.g. an optical switch or multiplexer to select the fibre in which the beam is to be sent.

Figure 1B:
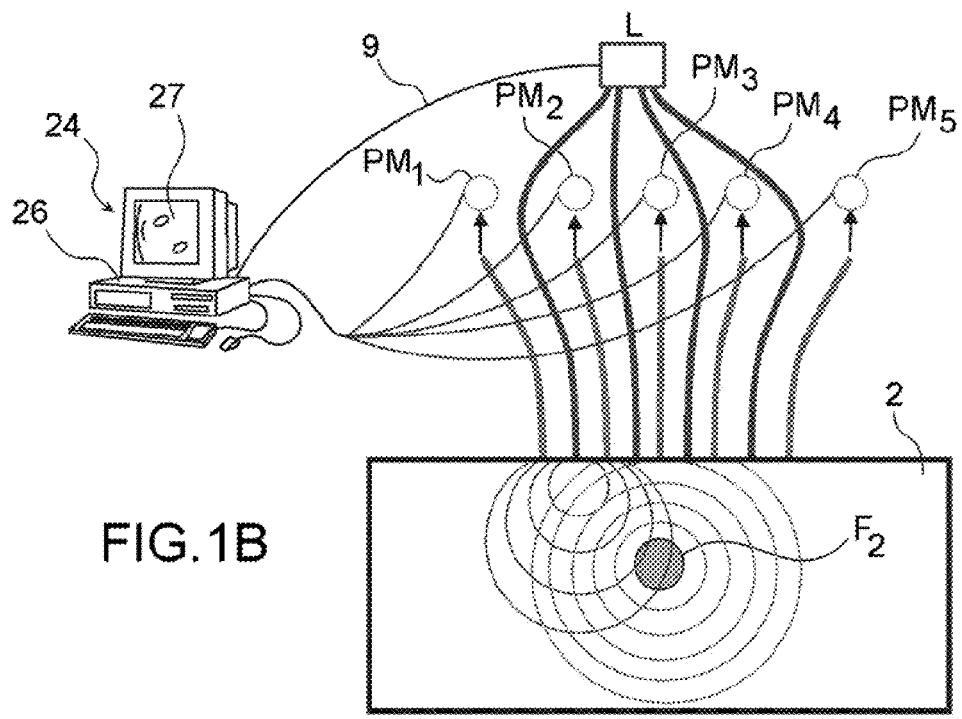
Figure 1C:
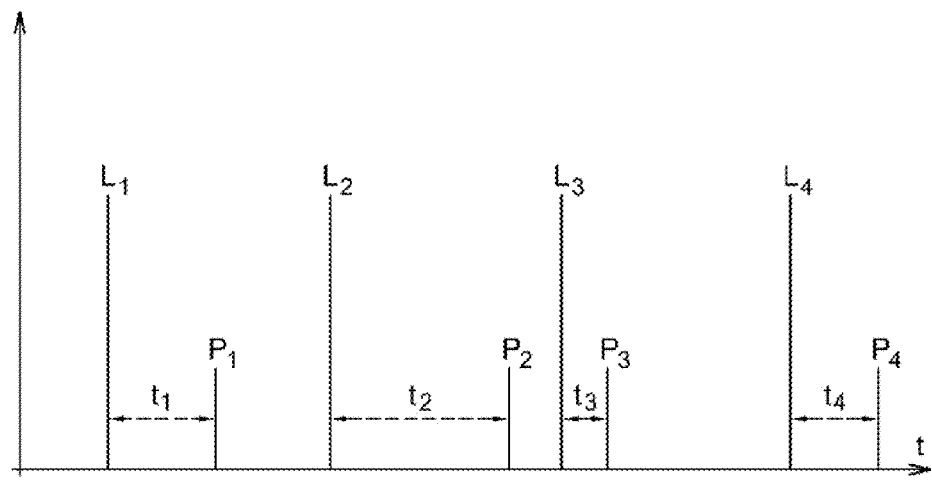
FIGS. 1C-1E respectively show a series of laser pulses and single emitted photons, and a fluorescence curve obtained from data on the single photons, and curves of measured fluorescence.

Each detector $D_i$ may comprise an array of camera pixels of CCD or CMOS type, or may comprise a photomultiplier, and it may be connected to an optical fibre which transmits the signal from the examined medium towards the detector, which is the case for the configuration in FIGS. 1A and 1B.

According to one embodiment, at the output of the detector(s), temporal analysis of the signals is performed using a dedicated measuring instrument (TCSPC—Time Correlated Single Photon Counting to count time correlated photons or intensified camera with temporal gate).

One of the pulse sources of radiation $L_i$ may also be used as means to trigger the TCSPC card (for example via a link $9_1$, $9_2$, 9 between each source $L_i$ and the means 24).

It is preferable to work with pulses in the femtosecond domain, provided the radiation source is adequate i.e. it comprises one or more laser sources $L_i$ each pulse of which has a temporal width also lying in the femtosecond domain. The use of pulsed sources of picosecond laser diode type can also be envisaged, the advantage of this solution being lower cost.

According to one particular embodiment, one or more sources $L_i$ are a pulsed laser diode, for example at a wavelength close to 630 nm and with a repeat rate of about 50 MHz.

The laser light preferably passes through an interference filter to remove any secondary modes. An interference filter and/or a coloured filter absorbing low wavelengths can be placed in front of each detector $PM_i$ or the tip $D_i$ of the corresponding fibre to select the fluorescence light (for example: $\lambda>650$ nm, the source being at a wavelength of 631 nm for example) of a fluorophore $F_i$ arranged in the medium 2 and to optimize elimination of the excitation light.

In the text of the present application, irrespective of the embodiment of the invention, one particular issue relates to the position of the radiation source and/or the position of the detection means.

When fibres are used, these positions are most often meant to be those of the tips of the fibres which convey the radiation into the diffusing medium 2, or to the interface of this medium and/or those which collect the diffused radiation, the latter being placed in the medium or at the interface with this medium, and in this case they are not to be understood as the positions of the source $L_i$ properly so-called or of the the detector $PM_i$ properly so-called. The fibres conveying the radiation into the medium can be called excitation fibres, and the fibres collecting the diffused radiation can be called emission fibres or collection fibres.

In applications of "endoscopy" type, use is preferably made of a fibre system, the fibres possibly being integrated in an endo-rectal probe for example, at least one fibre transmitting the source of pulsed excitation light towards the region to be examined.

This source of pulsed light may be external to the probe.

At least one other fibre transmits the optical emission signal of the region to be examined towards a photodetector which may also be external to the probe. With the Time Correlated Single Photon Counting technique (TCSPC), a photon is detected using a photomultiplier that is emitted by the fluorophore after a pulse of the radiation source.

The system therefore allows time-resolved detection of the fluorescence pulses.

It allows collection of the fluorescence photons.

FIG. 10 shows a series of laser pulses $I_i$ (i=1-4) and a series of corresponding single photons $p_i$ (i=1-4), these being detected by a TCSPC-type system (Time Correlated Single Photon Counting).

Each photon is in fact detected relative to the output of the corresponding pulse: in FIG. 10, $t_i$ represents the time elapsed between each laser pulse $I_i$ and the instant of detection of each photon $p_i$.

Figure 1D:
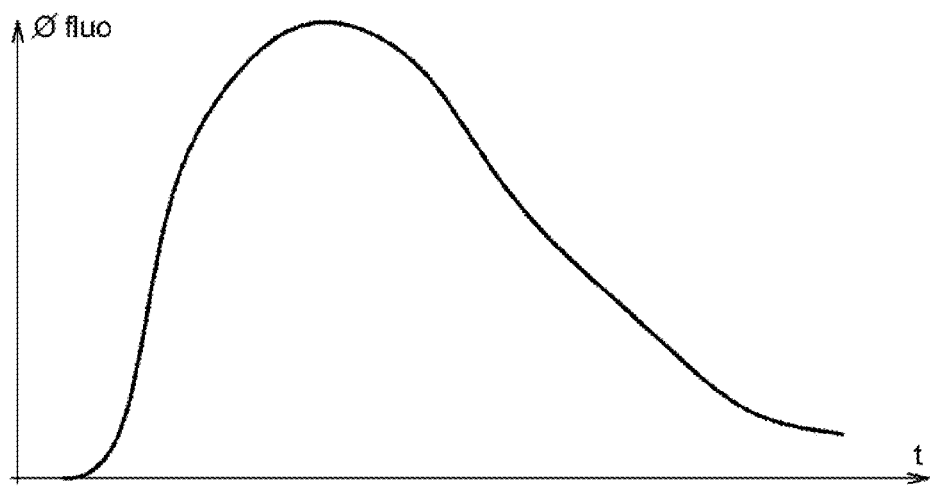

It is then possible to establish a statistical distribution or histogram of the photon arrival time, as illustrated in FIG. 1D, which shows the number of detected fluorescence photons, as a function of elapsed time t relative to each laser pulse. This histogram represents an experimental measurement of the function $M_{sd}(t)$ mentioned previously, this function $M_{sd}(t)$ being the theoretical histogram of photon arrival time. From said histogram, it is possible to determine statistical parameters, notably the intensity or mean arrival time, or mean time (in fact, the weighted mean of the abscissas with the ordinates of the histogram). Therefore, for each pair grouping together a source and a detector, called source-detector pair and denoted sd, this histogram can be obtained which is likened to the function $M_{sd}(t)$, after a large number of measurements or acquisitions.

Figure 1E:
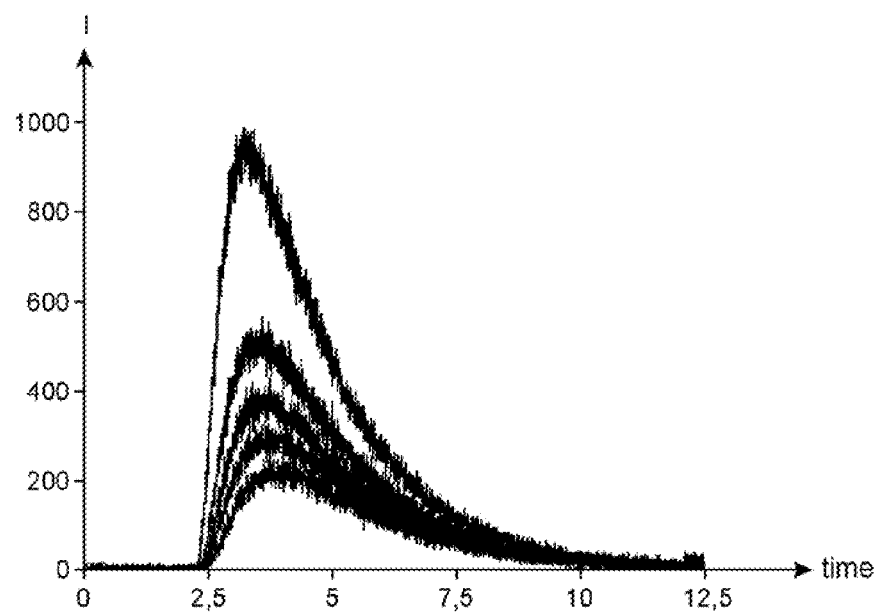

Said curve $M_{sd}$ (t) which, as can be seen (see also the example in FIG. 1E), allows all the information to be used over a wide time window either side of the point of maximum intensity (and not only in the rising part of the signal) can therefore be subsequently processed to obtain characteristic data such as arrival time, or mean time as will be explained below.

Electronic means 24 such as a microcomputer or computer are programmed to store in memory and process data derived from the detectors. More precisely, a central unit 26 is programmed to implement a processing method according to the invention: to compute one or more parameters $\chi^N_{i,m}$ or $\chi_{3,m}$ or one or more functions of these parameters and/or to apply a method such as described below for example in connection with one of FIG. 7 or 8. These means 26 can optionally be used to make one or more comparisons of the value(s) found for the parameter(s) with one or more threshold values.

An operator selects one or more of these parameters and/or one or more functions of these parameters, and computes the same to obtain initial data on a location of at least one fluorophore, optionally after comparing the computed results with one or more threshold values or with one or more minimum values or with one or more maximum values.

The electronic means 24 can optionally be used to control the triggering of the radiation source(s) and/or of the detector(s), for example for synchronization of all these means.

A monitoring screen or display or viewing means 27 can be used, after processing, to show the positioning of the fluorophore(s) in the examined medium 2. The means 24 and the display means 27 also enable an operator to determine a mesh such as used in the present application, as explained below.

If a locating result is not suitable or is not satisfactory, for example for lack of precision, at least one other parameter can be chosen or at least one iteration can be performed.

Other detection techniques can be used, for example with an intensified camera e.g. an ultra-rapid intensified camera of "gated camera" type; in this case, the camera opens onto a time gate of width about 200 ps for example, then this gate is shifted e.g. in steps of 25 ps.

The excitation light, at wavelength $\lambda_x$ excites the fluorophores $F_i$ which re-emit a so-called emission light at wavelength $\lambda_m > \lambda_x$ with a lifetime $\tau$. This lifetime corresponds to the mean duration during which the excited electrons remain in this state before returning to their initial state. For cases not concerning fluorescence imaging, the method can be used to locate absorbers in the medium i.e. sites at which the absorption coefficient of the medium is higher than the mean absorption coefficient of the medium. In the remainder of this application, said absorber can be likened to a fluorophore, by considering that its fluorescence wavelength, or emission wavelength, is equal to the excitation wavelength, and also by considering that the duration of fluorescence is zero, i.e $\tau=0$. In this case, the filter which may optionally be placed upstream of the detector is to be adapted to the excitation wavelength.

Irrespective of the medium and geometry under consideration one or more fluorescent inclusions are located in the medium, which has a light propagation velocity c $(=3*10^8$ m/s/n, n=optical index), a diffusion coefficient D and an absorption coefficient $\mu_a$.

The medium 2 surrounding the fluorophore $F_1$ may have any geometric shape; it may for example be of infinite type.

It may also be of semi-infinite type, limited by a wall. In this case, the excitation and emission optical fibres can be placed at the interface of the diffusing medium, or at a short depth of the order of a few mm.

A semi-infinite medium, in which each of the fibre tips conveying an excitation signal and collecting a fluorescence signal is arranged at more than 1 cm, or more than 1.5 cm or more than 2 cm from the wall limiting this medium can be treated, according to the method of the invention, as an infinite medium.

The surrounding medium may also form a slab limited by two parallel surfaces.

The invention also applies to a medium of any shape, whose outer surface is broken down into a series of planar facets.

In all cases, it is particularly well suited to the case of reflection geometry in which the source(s) and the detector(s) lie on the same face of the object or of the examined medium.

The Green functions $G_s(r,t)$ of a device according to the invention can be determined using a Monte-Carlo simulation, for example to solve the radiation transfer equation, or most often by solving the diffusion equation (1) to which boundary conditions are added (partial current boundary condition [Robin] or extrapolated boundary condition [Dirichlet]), as explained in the article by S. R. ARRIDGE: "Optical tomography in medical imaging", Inverse Problems, April 1999, vol. 15(2), R41-R93. These determinations or simulations can be carried out using computing means such as the means 26, 27 in FIGS. 1A and 1B. The moments of the Green functions Gs(r,t), such as defined previously (1'), can be obtained by iteratively solving equation (2).

According to one embodiment of the invention, a fluorophore is a single fluorophore $F_1$, or a plurality of fluorophores substantially grouped together in one same place.

According to another embodiment, the fluorophore comprises N fluorophores distributed in different places.

Using time-resolved optical measurements, it is sought to locate these fluorescent inclusions i.e. to reconstruct the fluorescence map.

According to the invention, the fluorescence map is reconstructed using an efficient method from a computing viewpoint, and which has the property of concentrating the fluorescence on small supports. The term "small supports" represents the fact that the fluorophore(s) are discretely distributed in certain places of the examined medium. The inventors considered that this type of prior information is well suited to the reconstruction of fluorophores in diffusing tissues, notably in some applications related to the early detection of cancerous tumours in organs such as the prostate, breast, testicles, brain, etc.

In one first embodiment, the case of a single fluorophore is considered.

Depending on the method used, the data on $M^0_{sd}$ and $M^1_{sd}$ is applied (already defined above, see for example Equations 11-14) to reconstruct the position of the fluorophores which emit fluorescence radiation.

In all cases, the fluorophore search volume is meshed into M mesh elements (or voxels) m, whose size depends on desired accuracy: the higher the precision the smaller the individual volume of a mesh element, and the greater the number of mesh elements.

This mesh can be decided by an operator of the computer system 24.

According to the invention, one or more first parameters $\chi_{im}$ are used called basic parameters (or criteria, but in the remainder hereof the expression "parameters" will be used) which are defined below, or a combination thereof, this combination then possibly being called a combined parameter Pm. According to this embodiment, the index m designates a voxel.

Each of these basic parameters depends on the variable m, and hence on the selected mesh element in the volume. All the mesh elements are selected one by one, and for each mesh element the parameter is computed which is a sum of the contributions of all the possible pairs (source-detector) of the system or part of all these pairs. In other words, each parameter represents the sum for different acquisitions, each acquisition corresponding to a source-detector-pair, of a combination between a magnitude (here and in the rest of this document this expression is equivalent to "function" or "quantity" or "parameter") determined from at least one moment of $M_{sd}(t)$, and the estimation of this magnitude, this estimation being made by considering a single fluorophore positioned in the voxel m.

By combination is meant any arithmetic operation, whether linear or not. It will be seen in the remainder of the description that this combination may assume the form of a subtraction or of a product for example.

It will also be seen that the magnitude determined from at least one moment of the function $M_{sd}(t)$ can be the zero-order moment of this function, or the first-order normalized moment, from which known and assumed constant temporal magnitudes (or "functions" or "parameters") are subtracted.

According to one preferred embodiment, this magnitude can be the zero-order moment of $M_{sd}(t)$, denoted $M^{(0)}_{sd}$.

Therefore, a first basic parameter $\chi_{1m}$ is defined:

$$\chi_{1m} = \min_{\alpha_m} \sum_{sd} \frac{(M^0_{sd} - \alpha_m \cdot G_{sm} G_{md})^2}{\sigma^2(M^0_{sd})}$$

$\chi_{1m}$, can be considered as a residual between the measurement of moment $M^{(0)}_{sd}$, and its estimation, given by the product $\alpha_m G_{sm} G_{md}$. $\chi_{1m}$ is minimal for the mesh elements m giving the best positioning of the fluorophore. Its value results from computing of the minimum value of the sum indicated above, for a set of coefficients $\alpha_m$. In other words, the set of coefficients $\alpha_m$ is sought which minimizes the above sum.

The term $\sigma^2(M_{sd}^0)$ shown in the denominator part is optional. It is an estimation of the uncertainty associated with the determination of $M_{sd}^0$. If $M_{sd}^0$ is the number of photons detected by the pair of detectors (s, d), and if the noise is Poissonian, then $\sigma^2(M_{sd}^0) = M_{sd}^0$ Therefore, each element $(M_{sd}^0 - \alpha_m G_{sm} G_{md})^2$ of the sum represents the difference between:

the value of the measured intensity $M_{sd}^0$ for the selected source-detector pair, when the source emits a pulse and the detector detects a fluorescence signal emitted by the fluorophore, and an estimation of the zero-order moment $M_{sd}^0$, obtained using the Green functions $G_{sm}$ and $G_{md}$, which can be estimated in the manner already described above, for example using means 24.

Again according to one preferred embodiment, the magnitude determined from at least one moment of $M_{sd}(t)$ is the first-order normalized moment, denoted $T_{sd}$, from which are subtracted the time of the function of the source Ts, the response time of the detector Td, and the fluorescence time τ. In this case, a second parameter $\chi_{2m}$ is used:

$$\chi_{2m} = \sum_{s,d} \frac{((T_{sd} - T_s - \tau - T_d) - (T_{sm} + T_{dm}))^2}{\sigma^2(T_{sd})}$$

$\chi_{2m}$, also called the criterion of time-of-flight measurement residual, is also small for mesh elements verifying good temporal agreement, and hence contributing towards better positioning of the fluorophore. More specifically, $\chi_{2m}$ corresponds to a difference (or residual), for at least one acquisition, between the mean measured source-detector time-of-flight (first-order normalized moment of M(t)) and this same, modelled, first-order normalized moment, the fluorophore then being assumed to correspond to the voxel m.

In the above expression of this parameter $\chi_{2m}$:

$T_{sd}$ is the measured source-detector time-of-flight, it is the first-order normalized moment of the measurement, $T_s$ is the mean time of the source function, previously mentioned;

$T_d$ is the response time of the detector, previously mentioned;

τ is the lifetime of the fluorophore;

$T_{sm}$ is the mean duration of the source-fluorophore trajectory (or source-voxel (m));

$T_{dm}$ is the mean duration of the fluorophore-detector trajectory (or detector-voxel (m)).

The term (Tsd−Ts−$T_d$−τ) represents the "net" time-of-flight, i.e. the measured time-of-flight, from which are subtracted the mean times of the source function, of detector response and of fluorescence lifetime. This net time-of-flight represents the duration of the light trajectory between the source, the fluorophore and the detector.

Tsm+Tdm represents an estimation of this net time-of-flight when the fluorophore is present in the voxel m.

The magnitudes $T_s$, $T_d$, τ are data which can be known: τ depends on the fluorophore, whilst the sum $T_s + T_d$ can be obtained by calibration testing as previously described. $T_{sm}$ and $T_{dm}$ are modelled either analytically or by solving equation (2), by considering that the fluorophore is single and located in the voxel m.

Preferably, and as is the case in the above formula, the parameter $\chi_{2m}$ can be normalized by a statistical magnitude (again, here and in the rest of the document, this expression is similar to "function" or "parameter") relative to the distribution of $T_{sd}$. This statistical magnitude acts as confidence indicator. Here $\sigma^2(T_{sd})$ has been chosen, but another statistical magnitude (e.g. standard deviation or variance) could be chosen, to indicate the confidence assigned to a distribution, but normalization by variance is optimal. This statistical magnitude is used to weight the measurements corresponding to a source-detector pair, relative to other measurements corresponding to another source-detector pair: the smaller the standard deviation of the distribution of $T_{sd}$, the more the measurements derived from this source-detector pair can be considered to be reliable and the greater the importance they can be given in determining the second coefficient, which is explained below. The magnitude $\sigma^2(T_{sd})$ can easily be estimated from a width $\Delta T_{sd}$ of function $M_{sd}(t)$ according to the following equations:

$$\Delta T_{sd} = \sqrt{\frac{\sum_i (t_i - T_{sd})^2 M_{sd}(t_i)}{M_{sd}^{(0)}}}$$

$$\sigma^2(T_{sd}) = \frac{\Delta T_{sd}^2}{M_{sd}^{(0)}}$$

where:

ti designates the abscissa i of function $M_{sd}(t)$

As for the first basic parameter $\chi_{1m}$, $\chi_{2m}$ is minimal for the mesh elements m in which the fluorophore is effectively positioned.

Therefore, when these two first parameters $\chi_{1m}$ and $\chi_{2m}$ are used, the mesh elements of the volume for which they are both minimum, are mesh elements in which the fluorophore may most probably be located.

Additionally, the inventors have evidenced the particular advantage of jointly using these two basic parameters $\chi_{1m}$ and $\chi_{2m}$. When the sources and detectors lie in a plane P (which is typically the case for a reflection configuration), the first basic parameter $\chi_{1m}$ gives particularly pertinent information on the coordinates of the fluorophore in this plane. In other words, the voxels m for which the coefficient $\chi_{1m}$ is minimum are generally distributed in a direction perpendicular to this plane, but their coordinates in this plane are little dispersed.

In complementary manner, and unexpectedly, the second basic parameter $\chi_{2m}$ gives particularly pertinent information on the position of the fluorophore in the direction perpendicular to this plane. For example, a parameter $\chi 2m$, combining a measurement and an estimation of the time-of-flight, gives an indication on the depth of the fluorophore in relation to a plane formed by the sources and detectors. In other words, the voxels m for which the coefficient $\chi_{2m}$ is minimum are generally distributed substantially parallel to the plane formed by the sources and detectors, and their coordinates in the direction perpendicular to this plane are little dispersed. These voxels are then located at one same depth in relation to the point at which the sources and detectors are located.

The advantage can therefore be appreciated of combining these two first basic parameters: the probability of the presence of the fluorophore in a voxel m will be higher the more the first basic parameter $\chi_{1m}$ and second basic parameter $\chi_{2m}$ are minimum for this voxel. Owing to the complementarity existing between these two first basic parameters $\chi_{1m}$ and $\chi_{2m}$, pertinent information will be obtained regarding the coordinates of the fluorophore in this plane defined by the sources and the detectors (by the first basic parameter $\chi_{1m}$), but also pertinent information regarding the coordinates of the fluorophore in the direction orthogonal to this plane i.e. to the depth (by the second basic parameter $\chi_{2m}$). The coordinates of the voxel likely to contain the fluorophore are thus defined.

A third basic parameter $\chi_{3m}$ can be formed by considering that the magnitude determined from the distribution Msd(t) is the zero-order moment, as for the determination of the first basic parameter. This magnitude is then combined with the estimation of this magnitude, said estimation being made by considering that the fluorophore is single and located in voxel m. But here this combination is not a difference but a correlation, in other words a product. Therefore, this third basic parameter corresponds to the correlation, for at least one source-detector pair, between a value of the measured intensity ($I_{sd} = M^{(0)}(t)$) determined by the zero-order moment of M(t), and a value of this estimated zero-order moment (the product $G_{sm} \cdot G_{dm}$). This coefficient of correlation corresponds to the sum, for each modelled source-detector pair, of the product between the measured value of $1_{sd}$ (intensity for one excitation by the source S and for one detection by the detector D) and the modelled intensity:

$$\chi_{3m} = \frac{\sum_{sd} I_{sd} G_{sm} G_{dm}}{\sqrt{\sum_{s,d} G_{sm}^2 \cdot G_{dm}^2}},$$

m being the index corresponding to the voxel under consideration, s and d representing the source and detector under consideration.

It is also possible to normalize this coefficient:

$$\frac{\sum_{sd} I_{sd} G_{sm} G_{dm}}{\sqrt{\sum_{s,d} G_{sm}^2 \cdot G_{dm}^2}}$$

using $$\chi_{3m} = \frac{\sum_{s,d} I_{sd} \cdot G_{sm} \cdot G_{dm}}{\sqrt{\sum_{s,d} I_{sd}^2} \cdot \sqrt{\sum_{s,d} G_{sm}^2 \cdot G_{dm}^2}}$$

this normalized coefficient then lying between 0 and 1.

Unlike the two preceding parameters, $\chi_{3m}$ is maximal for the mesh elements m giving the best positioning of the fluorophore, notably in a plane substantially parallel to the plane formed by the sources and detectors.

To implement a method according to the invention, at least one of the above basic parameters is chosen, and a combination $P_m$ is formed of these parameters. For example, Pm can be called a combined parameter, resulting from a combination of at least one first parameter (for only one parameter the term "function" of this parameter would best be used, but in the present application for reasons of simplification, the general expression "combination" will be used). Said combination Pm is also a function of m, i.e. of the voxel under consideration.

Said combination $P_m$ of these parameters, according to one preferred embodiment, can be the sum of the first and of the second basic parameters:

$\chi_{1m} + \chi_{2m}$

Therefore, when using this combined parameter $P_m = \chi_{1m} + \chi_{2m}$, the mesh elements of the volume for which $P_m$ is minimum are mesh elements in which the fluorophore may most probably be located.

Another example of a combination of the basic parameters can be the product of the first and second parameter for example:

$\chi_{1m} \cdot \chi_{2m}$

Here again, this combined parameter $P_m$ is minimum for the mesh element(s) in which the fluorophore is most probably located.

Yet another example of a combination of the basic parameters can be the ratio of the third and second basic parameters for example:

$\chi_{3m} / \chi_{2m}$

This combined parameter $P_m$ is maximum for the mesh element(s) in which the fluorophore is most probably located, since the third parameter is then minimum, whilst the second is maximum. On the other hand, it will be sought to maximize the inverse combined parameter $\chi_{2m}/\chi_{3m}$, if this is the one chosen as combined parameter.

It is also possible to choose only one parameter, a function of one of the above basic parameters, for example the square of one of these parameters, or its inverse.

To form a combined parameter, it is also possible to use at least two of the basic parameters, at least one thereof being the argument of a non-linear function. For example, it is possible to use the product $\chi_{1m}^2 \cdot \chi_{2m}$, the product of the square of the first by the second. Another example is the ratio $\chi_{2m}^2/\chi_{3m}$.

It is also possible to combine the three above parameters $\chi_{1m}$, $\chi_{2m}$ and $\chi_{3m}$ by taking into account the fact that the two first have their value increased, for a certain voxel, with the probability of presence of the fluorophore in this voxel, whilst the last one has its value decreased.

In this case of a single fluorophore, each value of the chosen basic parameter or combined parameter, for a given voxel, can be arranged in a vector X (M,1), each coordinate of the vector representing the value $P_m$ of the voxel m (1<i<m). Said vector can be called a fluorescence map.

Irrespective of the parameter chosen, whether a first basic parameter $\chi_{im}$ (i designating the index of the basic parameter) or a combined parameter Pm, it will be sought to determine whether it has a value higher or lower than a given value $P_{limite}$, to determine whether or not the corresponding voxel m is the one in which the fluorophore is probably or even most probably located. $P_{limite}$ for example is one half of the maximum value assumed by this parameter over all the voxels under consideration and, if the fluorophore is a single fluorophore, it is possible for example to choose the voxel for which the parameter has the maximum value.

As a variant, $P_{limite}$ is at least equal to one half of the maximum value assumed by this parameter over all the voxels under consideration and, if the fluorophore is a single fluorophore, it is possible for example to choose the voxel for which the parameter has the minimum value.

In relation to the value that the chosen parameter assumes for a given voxel $m_0$, this voxel may appear in an image representing the medium under consideration, for example on the screen 27, with a certain colour scale in relation to the value of $P_{m0}$. As a variant, it is only the voxels for which the chosen parameter is greater or lower than the selected threshold value which will be shown in this image.

According to one example of embodiment, the parameter $\chi_{3m}/\chi_{2m}$, is used, the ratio of the third to the second.

Figure 2:
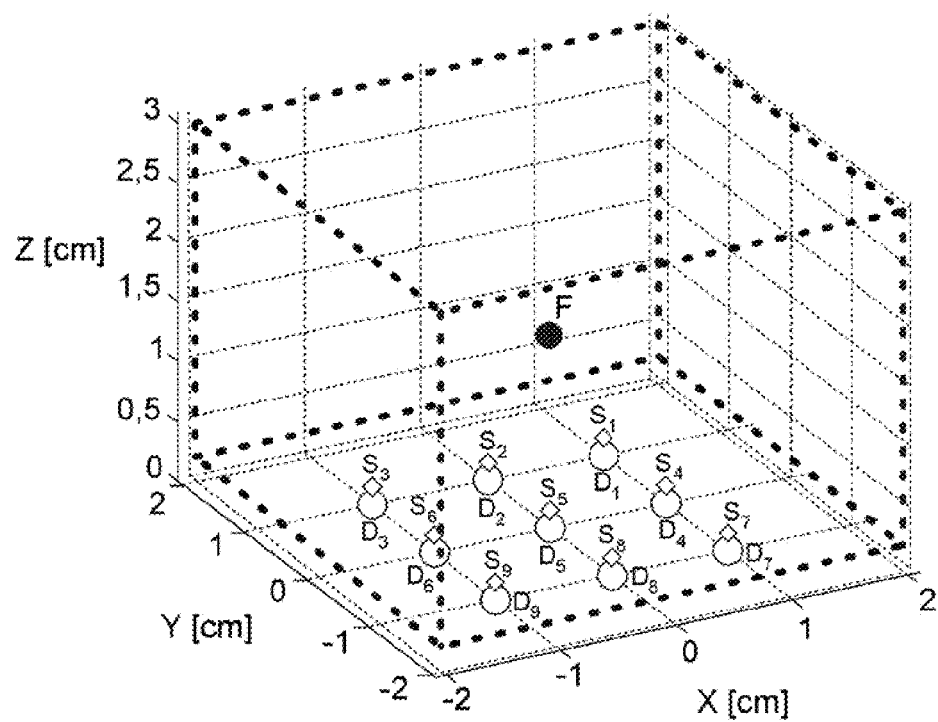
FIG. 2 is a schematic of a configuration of fluorophores, sources and detectors used for tests.

The example is taken of the configuration in FIG. 2 which is a schematic of a configuration used for tests; this configuration comprises 3×3 sources $S_1$-$S_9$, positioned in plane z=0, and 3×3 detectors $D_1$-$D_9$, positioned in the same plane as the sources. The fluorophore F is positioned in the plane z=1.6 cm.

Illumination is carried out with the 9 sources and a fluorescence signal is formed by the 9 detectors.

Figure 3A:
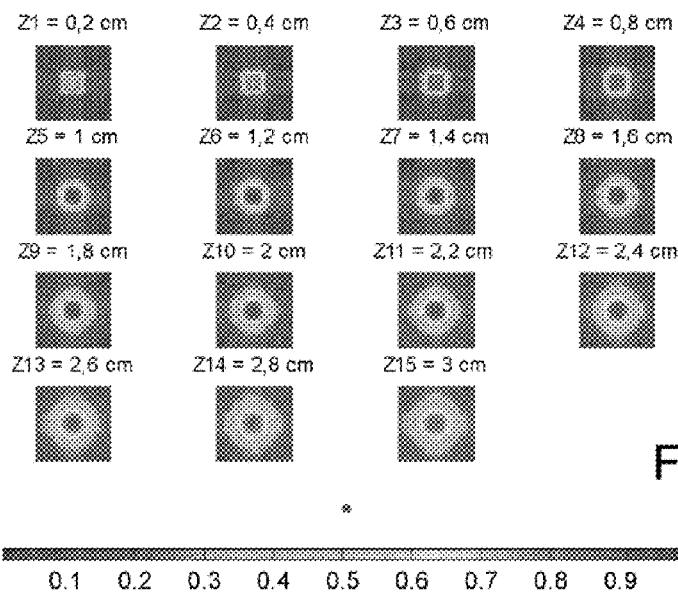
FIGS. 3A-3C, 4A-4C illustrate the application of non-combined criteria, according to the invention.
Figure 3B:
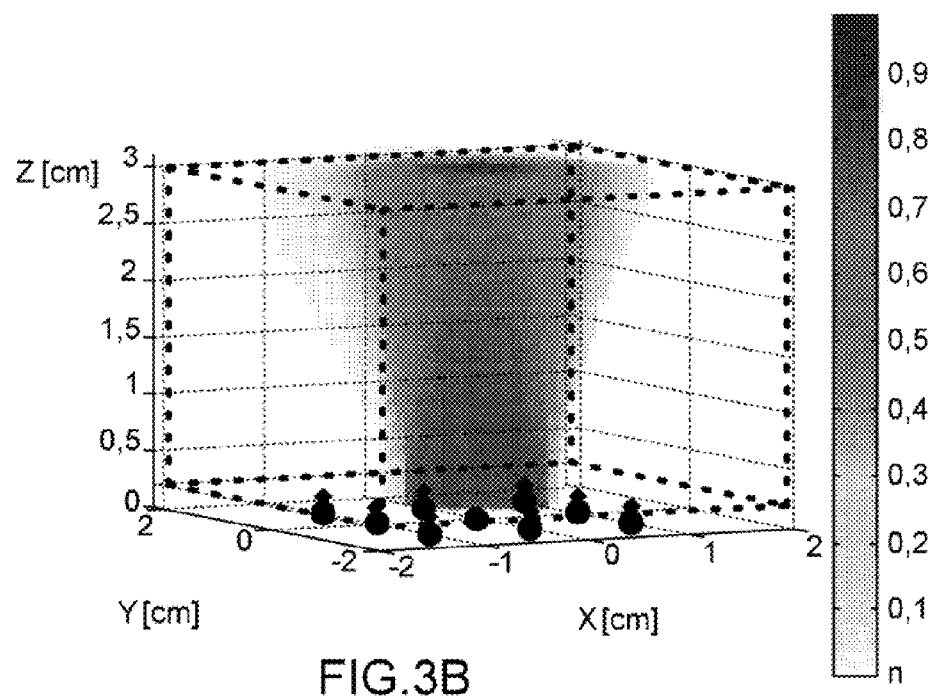

The method presented above is applied to this configuration in FIG. 2, only the basic parameter $\chi_{3m}$ being chosen, the map of correlations in FIGS. 3A and 3B is obtained.

It can notably be seen in FIG. 3B, that the position is relatively well determined along axes x and y. However, the position along z is not at all precise. FIG. 3A shows slices of FIG. 3B at different altitudes of z: the identified region for location of the fluorophore appears as a lighter region: this region extends along direction z, which is why its trace can be seen at different altitudes z in FIG. 3A (the principle is the same in FIGS. 4A, 5A, 5B, 11C and 12C described below).

Figure 3C:
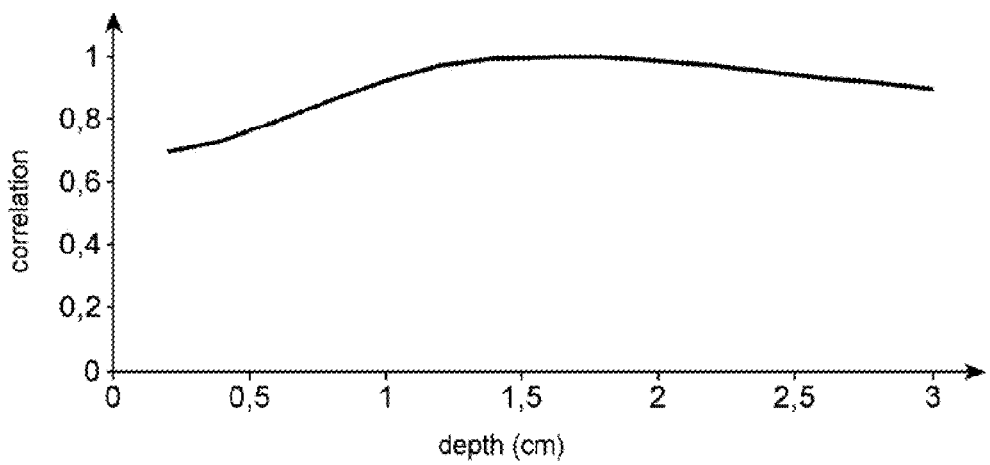

FIG. 3C illustrates the value of $\chi_{3m}$ in relation to depth, along a vertical straight line (parallel to z) and passing through the fluorophore. The shape of the resulting curve, very flat, confirms this lack of precision: the parameter $\chi_{3m}$ has almost the same value everywhere, this value is close to 1, therefore the fluorophore can be everywhere.

Figure 4A:
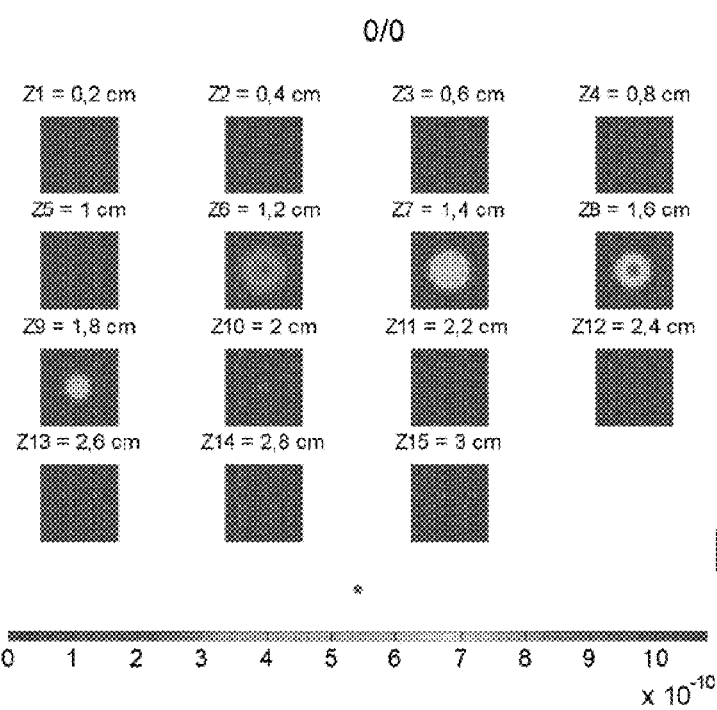
Figure 4B:
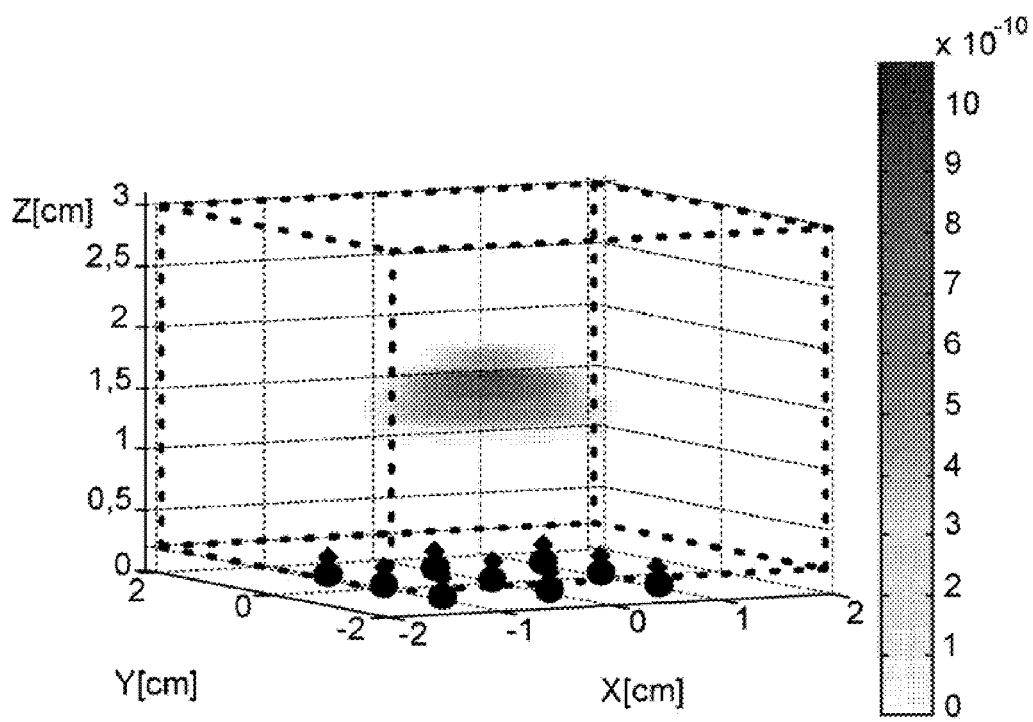

The map of criterion $-\chi_{2m}$, with a factor $\sigma_m$ taken to be constant and equal to 1 for the needs of the simulation, is illustrated in FIGS. 4A and 4B. More exactly, it is the criterion max $(-\chi_{2m})/6-\chi_{2m}$ which is shown, limited to the positive values. FIG. 4A shows slices of FIG. 4B at different altitudes of z.

It can be seen in FIG. 4B that this time a more precise result is obtained along z than along x and y.

Figure 4C:
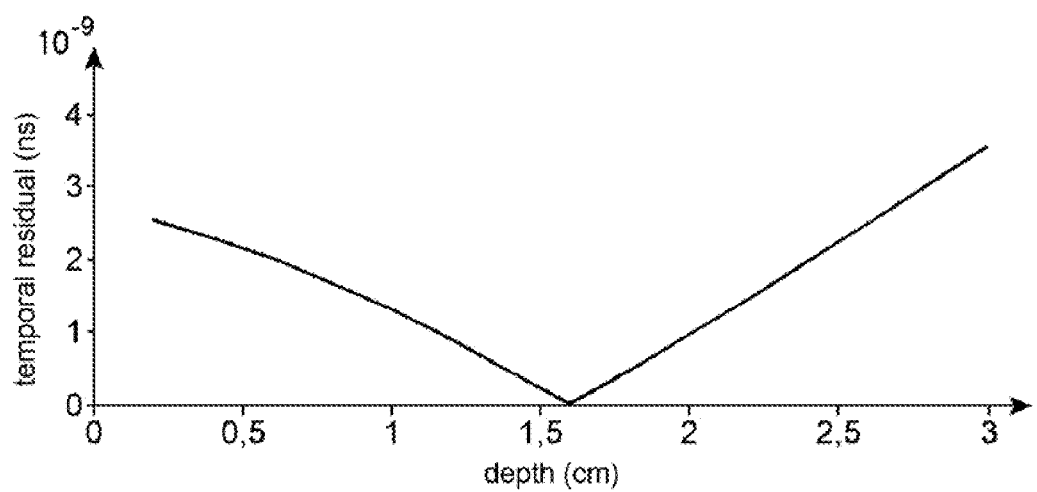
Figure 5A:
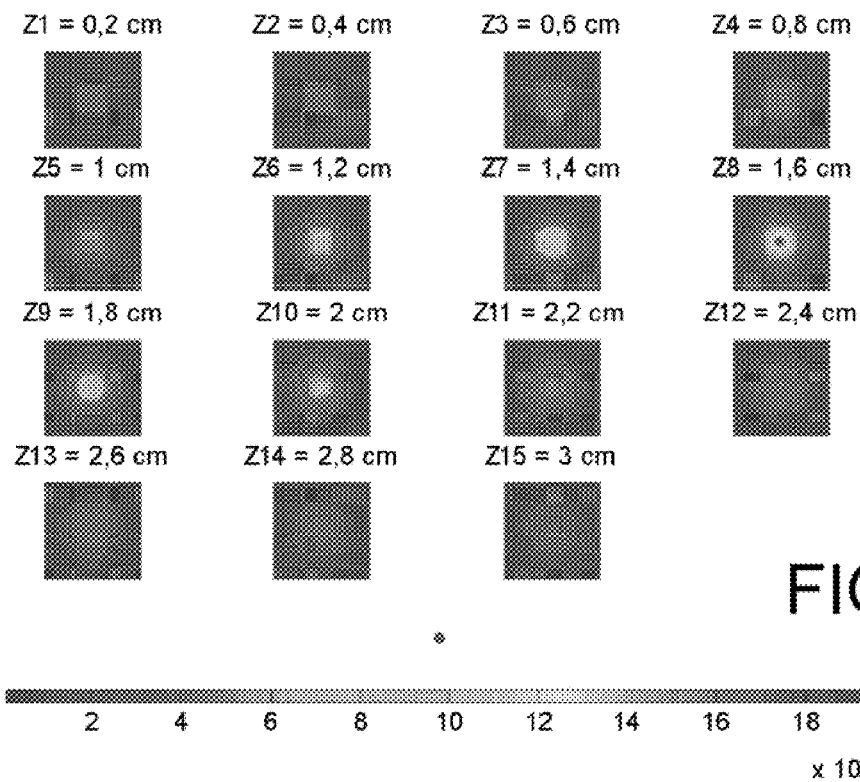
FIGS. 5A-5B illustrate the application of a combined criterion according to the invention.
Figure 5B:
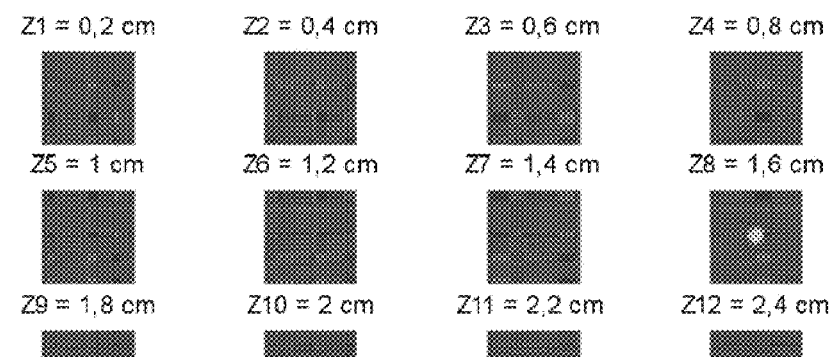

FIG. 4C illustrates the value of the combined parameter $P_{m1}=\max(-\chi_{2m})/6-\chi_{2m}$ in relation to depth, along a vertical straight line (parallel to z) and passing through the fluorophore. The shape of the resulting curve, minimum in the vicinity of a particular value (here close to z=1.5 cm), shows that precise location along z can be obtained by using this combined parameter.

It is also possible to use a parameter $p_m$ which combines the two above parameters. For example:

$$P_{m2}=\chi_{3m}/\chi_{2m},$$

This gives a precise result both in planes x, y but also in plane z, as illustrated in FIGS. 5A and 5B, which again are successive slices at different altitudes z.

It can be seen that it was therefore possible to position the fluorophore correctly.

Although a description has been given here of the determination of parameters $\chi_{1m}$, $\chi_{2m}$ and $\chi_{3m}$, from the zero-order moment or from the first-order normalized moment of at least one distribution $M_{sd}(t)$, it will be appreciated that other basic parameters could be determined, combining firstly a magnitude determined from at least one moment of $M_{sd}(t)$, and secondly an estimation of this magnitude, this estimation being performed by considering that the fluorophore is a single fluorophore and located in voxel m.

In another embodiment, the case is treated of N (>1) fluorophores, N being a known number.

Figure 6:
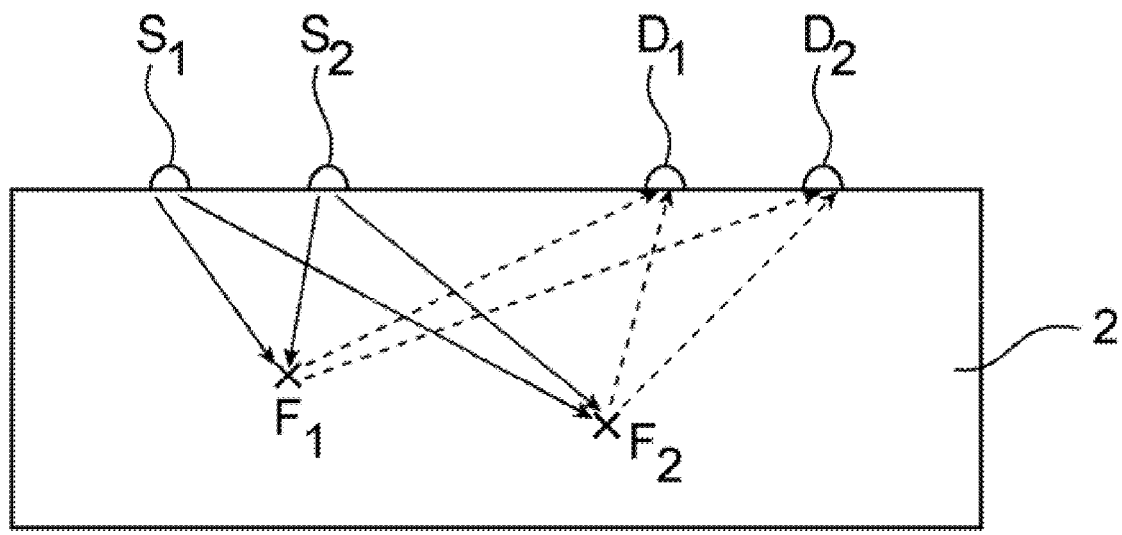
FIG. 6 schematically illustrates a configuration of 2 fluorophores, 2 sources and 2 detectors.

This case is illustrated in FIG. 6, in which a medium 2 contains 2 fluorophores $F_1$, $F_2$ and is provided with two sources $S_1$, $S_2$ and 2 detectors $D_1$, $D_2$ to detect the fluorescence emitted by the fluorophores.

When illumination is produced by the source $S_1$, excitation of the 2 fluorophores occurs, which each re-emit fluorescence radiation captured by the detectors $D_1$, $D_2$.

The same applies when illumination is produced by the source $S_2$: the signal of each of the two detectors contains a contribution of each of the two fluorophores.

The purpose is therefore to be able to identify the positions of the two fluorophores $F_1$ and $F_2$ using the signals produced by the two detectors $D_1$, $D_2$.

The starting points are the intensities and times-of-flight determined from the signals provided by the two detectors.

For each fluorophore, it is then proceeded with computing or estimating one or more basic or combined parameters having the same form as those already described above. But consideration is given to the values of these same parameters which have already been computed for one or more other fluorophores.

In other words, in the formulas which give the values of the basic parameters, the values of moments $M^{(0)}_{sd}$ and $M^{(1)}_{sd}$ for each source-detector pair will be replaced by a corrected value $M'^{(0)}_{sd}$ and $M'^{(1)}_{sd}$ which takes into account the contributions of already identified fluorophores. The corrected values are equal to the difference between the measured moments and the estimated contribution to these moments by already identified or located fluorophores. Procedure is therefore via iteration.

In this variant of the method according to the invention, applied to the case of N fluorophores, a matrix X(M,N) is reconstructed, N being the number of fluorophores, M being the number of voxels. Each element of the matrix $X_{mn}$ represents the combined coefficient $P_m$ corresponding to the voxel m (1<m<M) and to the fluorophore n (1<n≦N). This matrix is an association of N column vectors X(M, 1), i.e. of N fluorescence maps.

As above, the measurements $M_{sd}(t)$ corresponding to different source-detector pairs are performed previously, which allows determination of the moments $M^{(0)}_{sd}$ and $M^{(1)}_{sd}$ for each source-detector pair.

The method is now explained in connection with FIG. 7.

Initially (S0), all the elements of the matrix are initialized to 0. N is known (number of fluorophores present in the diffusing medium based on prior information) and M is also known (number of voxels discretizing the medium).

For each value of n:
first the coefficients (1≦m≦M) of column n are set at 0 (step S1);
the remainder of the measurements is computed (step S2) from the above formulas 10 and 12, discretized onto a mesh whose elements are indexed by m):

$$M'^{(0)}_{sd} = M^{(0)}_{sd} - S^{(0)} D^{(0)} \sum_m \sum_n \cdot G_{sm} \cdot X_{mn} \cdot G_{md}$$

$$M'^{(1)}_{sd} = M^{(1)}_{sd} - S^{(0)} D^{(0)} \sum_m \sum_n \cdot G_{sm} \cdot X_{mn} \cdot G_{md} \cdot (T_s + T_{sm} + \tau + T_{md} + T_d)$$

In these formulas $G_{sm}$ and $G_{md}$ are the simulated Green functions (already mentioned above) and $X_{mn}$ is the element (m,n) of the matrix X, previously initialized to 0, but comprising terms already estimated if n>1; $M'^{(0)}_{sd}$ and $M'^{(1)}_{sd}$ are forced to be strictly positive, by zeroing strictly negative values (step S3). $S^{(0)}$ and $D^{(0)}$ have already been defined.

Each value of $M'^{(0)}_{sd}$ is the difference between the measured value of $M^{(0)}_{sd}$ and the estimated value using the $G_{sm}$ and $G_{md}$ values applied to the current coefficient $X_{mn}$, such as results from the preceding iteration (optionally from the initial zeroing).

It can also be said:
that $M'^{(0)}_{sd}$ is the measured intensity $M_{sd}^0$ for each selected source-detector pair, corrected by the estimation of the contribution to intensity by already located fluorophores for each of which at least one coefficient of the corresponding column of the matrix X is nonzero;
whilst $M'^{(1)}_{sd}$ is the mean measured source-detector first-order moment (first-order normalized moment of M(t)), corrected by the estimation of time-of-flight contribution by already located fluorophores for each of which, here again, at least one coefficient of the corresponding column of the matrix X is nonzero.

It is then possible (step S4), for each voxel m and using $M'^{(0)}_{sd}$ and $M'^{(1)}_{sd}$, to determine at least one of the basic parameters $\chi_{im}$ (for example $\chi_{1m}, \chi_{2m}, \chi_{3m}$) and optionally at least one combined parameter $P_m$, $P_m$ having the form already defined previously for the case when there is only a single fluorophore.

Therefore, $\chi_{1m}$ is determined by replacing $M^{(0)}_{sd}$ by $M'^{(0)}_{sd}$ and $\chi_{2m}$ is determined by replacing $T_{sd}$ by $M'^{(1)}_{sd}/M'^{(0)}_{sd}$, whilst $\chi_{3m}$ is determined by replacing $I_{sd}$ by $M'^{(0)}_{sd}$ Therefore n being fixed, for every m (step S5):
$X(m,n) = P_m$ or $\chi_{im}$ or $\chi'_{im}$ (i=1–3).

It is optionally possible to proceed with adjusting the terms of the matrix X (step S6) by assigning a multiplicative coefficient $\alpha_i$ to each of the N columns of the matrix X being formed, by endeavouring to cause the following sum to converge towards $M^{(0)}_{sd}$:

$$\sum_m \sum_n G_{sm} X_{mn} G_{md} \alpha_n \approx M^{(0)}_{sd}$$

Convergence can be obtained using a least square method. This step allows a significant improvement in the quality of results.

Matrix X is adjusted by multiplying each term of a column n by the coefficient $\alpha_n$. It is specified that these coefficients $\alpha_n$ can be considered to be the intensities of the fluorescence signal.

Next, n is incremented (step S7) and a return is made to step S1 (in which all the elements of the column n are initialized to 0). If there is no convergence test step S6, S5 is followed by S7.

When the matrix X has been formed (n=N, step S7) by the preceding loop, it can be verified (step S8) that $$\sum_m \sum_n G_{sm} X_{mn} G_{md} \alpha_n$$

is close to $M_{sd}^{(0)}$.

If the correlation is not satisfactory, the above loop is reiterated from step S2 using X, which has just been computed, as the initial matrix. Correlation, for example, may comprise a so-called residual difference test with respect to data, corresponding to the determination of a difference between an estimated magnitude and an effectively measured magnitude.

Here, the estimated magnitude is:

$$\sum_m \sum_n G_{sm} X_{mn} G_{md} \alpha_n$$

for the measured magnitude $M_{sd}^{(0)}$.
The estimated magnitude is:

$$\frac{\sum_m \sum_n G_{sm} X_{mn} G_{md} (Ts + Tsm + Tm + Tmd + Td)}{\sum_m \sum_n G_{sm} X_{mn} G_{md} \alpha_n}$$

for the measured magnitude $M_{sd}^{(1)}/M_{sd}^{(0)}$

Finally, here again, in each column i.e. for each fluorophore, the row m is selected for which the basic parameter $\chi_{im}$ or combined parameter Pm, gives the minimum or maximum value, depending on the type of this parameter: as already explained above, for each of the parameters $\chi_{1m}, \chi_{2m}$ the maximum value is taken, and for parameter $\chi_{3m}$ the minimum value; these principles are applied to every combined parameter which results from these basic parameters.

The selected row m corresponds to a voxel m in which the fluorophore n is probably or most probably located.

Another embodiment treats the case in which N (>1) fluorophores, N being an unknown integer.

Physically, the situation is substantially the same as the one already described above in connection with FIG. 6 and with the preceding case.

However, the number of fluorophores is unknown, and hence the number of columns which the matrix X must have.

Iteration is also performed, using the same parameters already presented $\chi_{1m}$, $\chi_{2m}$, $\chi_{3m}$ and optionally at least one combined parameter $P_m$.

This variant of the method is now explained with reference to FIG. 8.

N, the number of fluorophores, is initialized to 0 (step S'0), then it is incremented to 1 (step S'1).

Next, (step S'2), all the elements of the matrix are initialized to 0. Only M is known (number of voxels discretizing the medium).

Then $N_{iter}$, the number of iterations, is initialized to 0 (step S'3), after which it is incremented to 1 (step S'4). During the initialization of $N_{iter}$, it is also possible to determine the maximum number of iterations it is desired to perform.

Steps S'5-S'11 are identical to steps S2-S8. Reference is therefore to be made to the above description.

If the correlation is satisfactory, the number of fluorophores is equal to the current number N and the matrix X is formed of the previously determined elements (step S'12).

This leads to the end of the method (step S'13).

If the correlation is not satisfactory, it is checked whether the number of iterations is the previously fixed maximum number $N_{iter}$ (step S'11).

If this is not the case, it is returned to step S'3 by incrementing $N_{iter}$ by one unit.

If it is the case, insofar as the correlation test has failed, the number of fluorophores is incremented by one unit (return to step S'1).

The method is continued until a matrix has been determined for which the correlation test is satisfactory (S'1-S'13).

Finally here again, in each column i.e. for each fluorophore, the row m is selected for which the basic or combined parameter gives the minimum or maximum value, depending on the nature of this parameter: as already explained above, for each of the parameters $\chi_{1m}$, $\chi_{2m}$ the maximum value is taken and for parameter $\chi_{3m}$ the minimum value; and these principles are applied to every combined parameter which results from these basic parameters. The selected row corresponds to a voxel m in which the fluorophore n is probably or most probably located.

One variant of this method for an unknown number N of fluorophores can be the following:

1) N=1 is used,
2) the reconstruction described above with reference to FIG. 7 is applied for N fluorophores,
3) testing to determine whether data attachment is satisfactory,
4) if yes, end; If not N=N+1, and it is returned to step 2.

An example is now given with two fluorophores.

Figure 7:
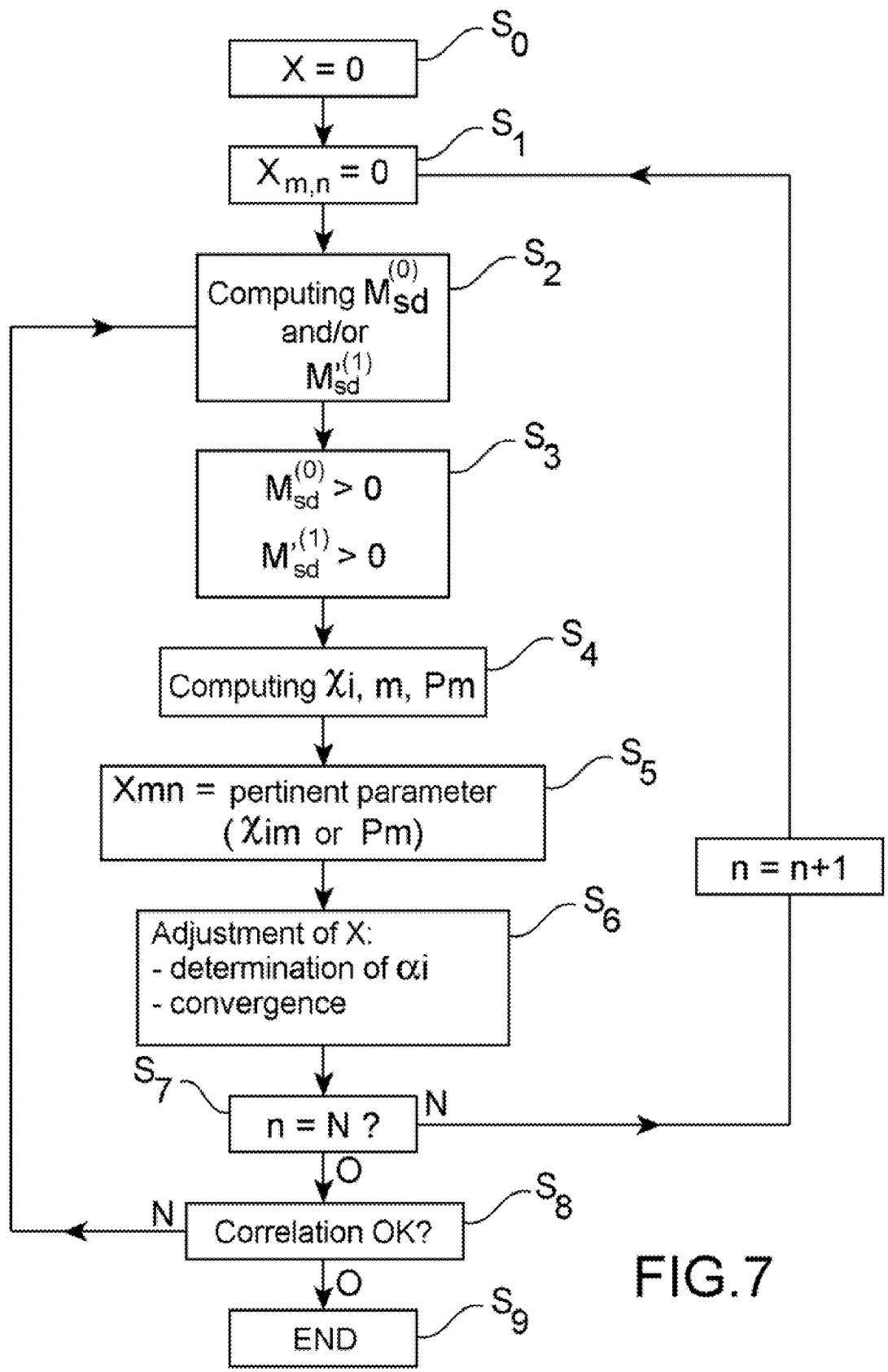

The method in FIG. 7 is applied.

Figure 9A:
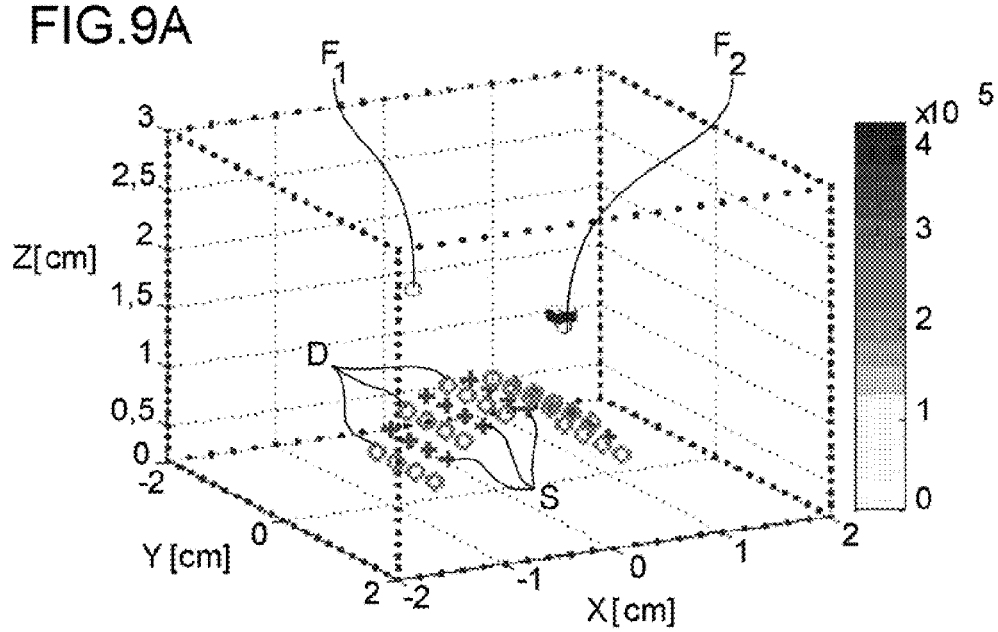
FIGS. 9A-9C and 10A-10H illustrate examples of application of a method according to the invention.

The two fluorophores are designated $F_1$ and $F_2$ in FIG. 9A. The sources S and detectors D are arranged on a cylindrical surface as can be seen in this figure.

Figure 9B:
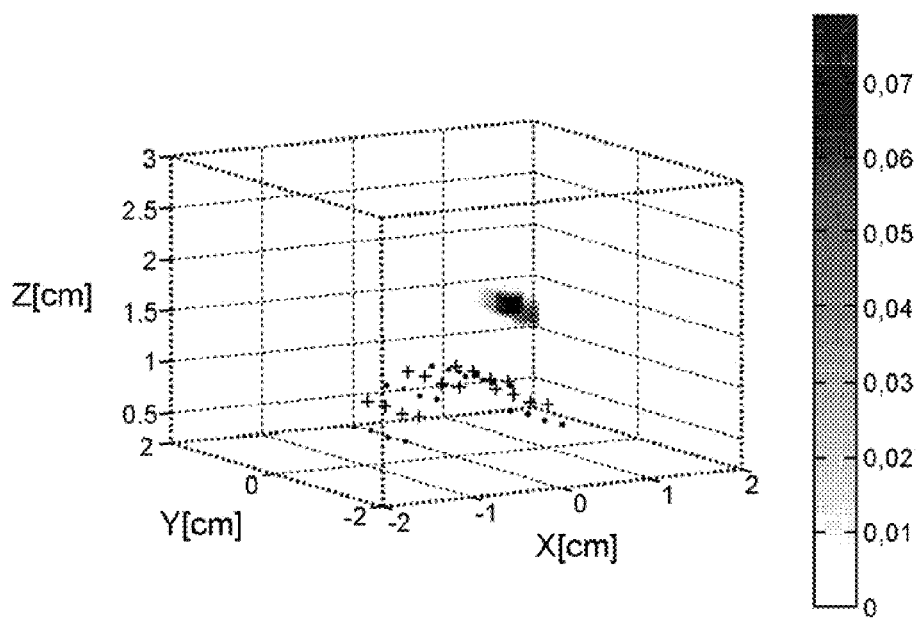

During iteration 1, it can be seen (FIG. 9B) that one of the fluorophores is correctly reconstructed. FIGS. 10A-10D show representations of $M^{(0)}{}_{exp}$ (measurement of $M^{(0)}$, FIG. 10A), $M^{(1)}{}_{exp}$ (measurement de $M^{(1)}$, FIG. 10B), $M^{(0)}{}_{est}$ (computing of $M^{(0)}$, FIG. 10C), $M^{(1)}{}_{est}$ (computing of $M^{(1)}$, FIG. 10D). These figures show that the convergence of estimations towards measured data is not satisfactory.

Figure 9C:
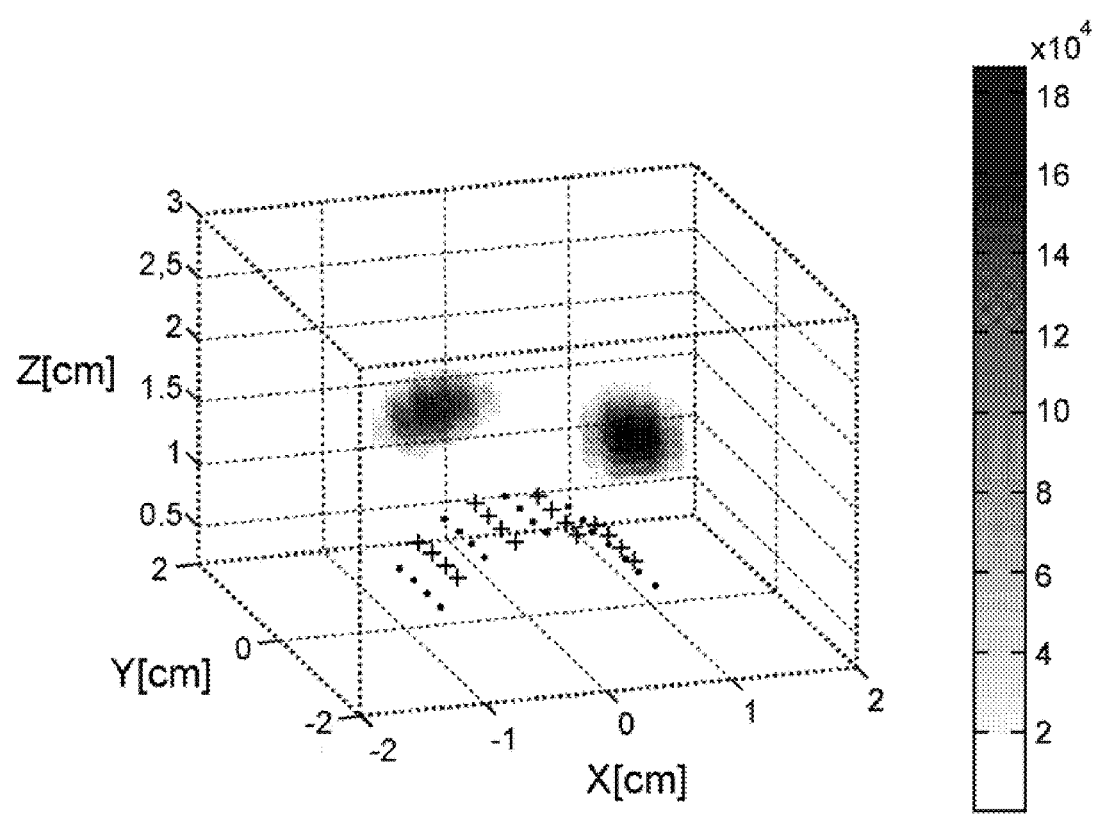
Figure 10A:
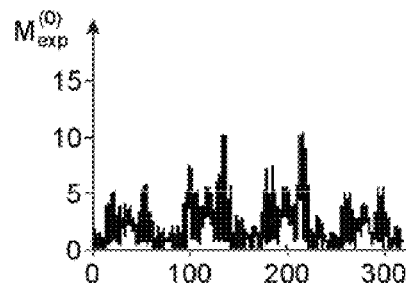
Figure 10B:
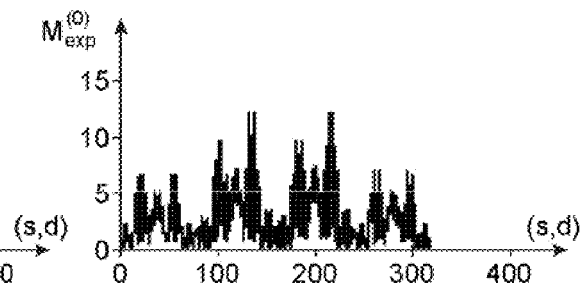
Figure 10C:
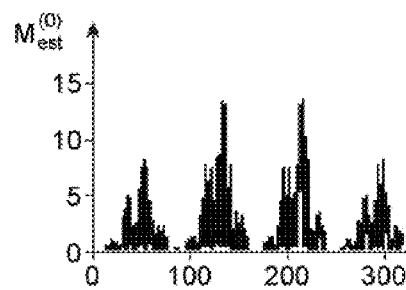
Figure 10D:
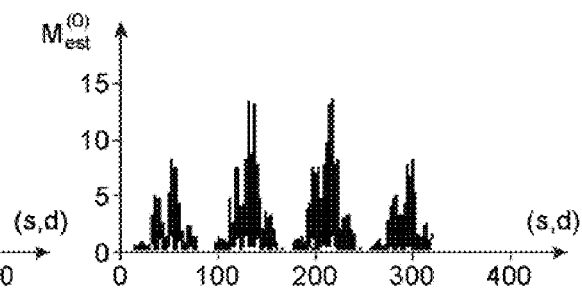
Figure 10E:
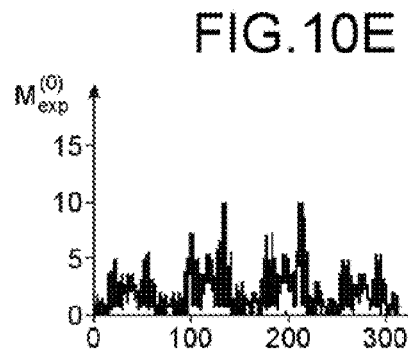
Figure 10F:
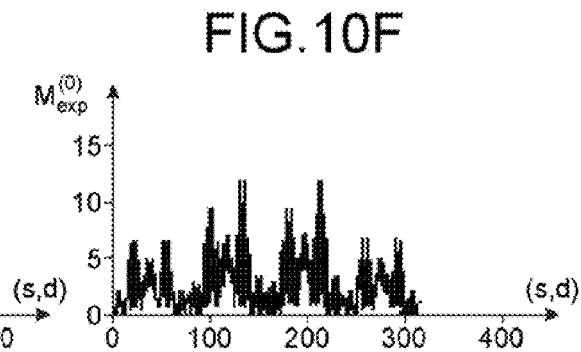
Figure 10G:
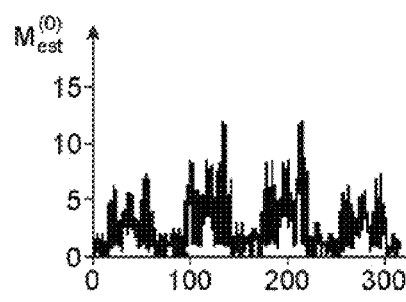
Figure 10H:
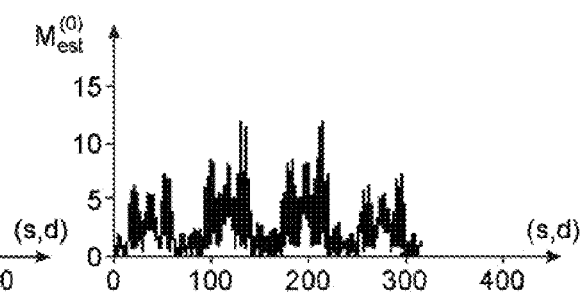

During iteration 2, it can be seen (FIG. 9C) that both fluorophores are correctly reconstructed. FIGS. 10E-10H show representations of $M^{(0)}{}_{exp}$ (measurement of $M^{(0)}$, FIG. 10E), $M^{(1)}{}_{exp}$ (measurement of $M^{(1)}$, FIG. 10F), $M^{(0)}{}_{est}$ (computing of $M^{(0)}$, FIG. 10G), $M^{(1)}{}_{est}$ (computing of $M^{(1)}$, FIG. 10H). These figures show that the convergence of estimations towards measured data is satisfactory.

A fourth embodiment corresponds to a generalization of the first embodiment. In the latter, it was seen that it is possible to determine basic coefficients $\chi_{im}$ performing a sum for different acquisitions, each acquisition corresponding to a source-detector pair, of a combination between a magnitude determined from at least one moment of $M_{sd}(t)$, and the estimation of this magnitude, this estimation being made by considering a single fluorophore positioned in the voxel m.

Therefore, according to this first embodiment, during the determination of each basic coefficient $\chi_{im}$, it was considered that a configuration is assumed a priori in which the fluorophore is single and located in the voxel m.

According to this fourth embodiment, basic coefficients $\chi_{im}$ are also determined similar to those described in the first embodiment, but when determining the basic coefficients $\chi_{im}{}^N$, an a priori configuration is taken in which there are N fluorophores located in N different voxels. The index m then corresponds to a configuration i.e. a particular distribution of these N fluorophores among the M voxels in which the examined medium has been discretized.

It can therefore be understood that there are $M^N$ possible configurations (maximum). Therefore it is possible to determine $M^N$ n-th basic parameters $\chi_{im}{}^N$.

The first embodiment may correspond to a particular case of this fourth embodiment in which N=1: there are therefore M parameters $\chi_{im}{}^{N=1}$ which can be determined, the index m corresponding to a particular distribution of the single fluorophore among the M voxels of the medium: the distribution in which the fluorophore is located in the voxel m.

Therefore, if N fluorophores are considered, N being a natural strictly positive integer, it is possible to determine at least one basic parameter $\chi_{im}{}^N$, which, for at least one acquisition Msd(t) corresponding to a source-detector pair, is equal to the combination of a magnitude obtained from at least one moment of Msd(t) with an estimation of said magnitude, this estimation being made by considering that the N fluorophores are distributed over the M voxels of the medium in a given distribution, said distribution being indexed by the parameter m.

Therefore, each i-th basic coefficient $\chi_{im}$ is obtained by considering a given distribution m of the N fluorophores in the M voxels. As recalled above, there are therefore $M^N$ possible distributions, corresponding to as many i-th possible basic coefficients. In other words, $1 \leq m \leq M^N$ If it is considered that the magnitude obtained from at least one moment of $M_{sd}(t)$ is a zero-order moment of $M_{sd}(t)$, denoted $M_{sd}{}^{(0)}$, it is therefore possible to determine a first basic coefficient $\chi_{1m}{}^N$ such that:

$$\chi_{1m}^N = \min_{\alpha_1,\ldots\alpha_N} \sum_{sd} \frac{(M_{sd}^{(0)} - M_{sd,m}^{theo0}(\alpha_1,\ldots\alpha_N))^2}{\sigma^2(M_{sd}^0)}$$

-continued where:

$$M_{sd,m}^{theo0}(\alpha_1, \ldots \alpha_N) = \sum_{n=1}^{N} \alpha_n G_{sm_n} G_{m_n d}$$

A configuration m is considered here which corresponds to N fluorophores distributed in the voxels $m_n$, $1 \leq n \leq N$.

$G_{smn}$ (respectively $G_{mnd}$) represent the energy transfer functions between the source and the voxel $m_n$ (respectively the voxel $m_n$ and the detector d). The coefficients $\alpha_n$, which can be considered as intensities, are obtained by the minimization operation, as is $\chi_{1m}$.

Each element $(M_{sd}^0 - M_{sd,m}^{theo0}(\alpha_1, \ldots \alpha_N))$ of the sum then represents the difference or more generally the comparison (it could well be a ratio) between:

the value of the measured intensity $M_{sd}^0$ for the selected source-detector pair, and an estimation of the zero-order moment $M_{sd}^0$, obtained using firstly the Green functions $G_{smn}$ and $G_{mnd}$ which can be estimated in the manner already described above, and secondly a set of coefficients $\alpha_n$ each of which is assigned to a fluorophore and which represents the fluorescence emission intensity thereof.

This first basic parameter $\chi_{1m}^N$ is minimum for the configurations m the closest to the real distribution of the N fluorophores in the examined medium.

If it is considered that the magnitude obtained from at least one moment of $M_{sd}(t)$ is a first-order normalized moment of $M_{sd}(t)$, denoted $M_{sd}^{(1)}/M_{sd}^{(0)}$, possibly also being denoted $T_{sd}$, from which the known temporal magnitudes Ts (mean time of the source), Td (response time of the detector) and $\sigma$ (duration of fluorescence) may optionally be subtracted, it is then possible to determine a second basic parameter $\chi_{2m}$ such that:

$$\chi_{2m}^N = \min_{\alpha'_1, \ldots \alpha'_N} \sum_{sd} \frac{((T_{sd} - T_s - \sigma - T_d) - (T_{sd,m}^{theo}(\alpha'_1, \ldots \alpha'_N)))^2}{\sigma^2(T_{sd})}$$

where:

$$T_{sd,m}^{theo}(\alpha'_1, \ldots \alpha'_N) = \frac{\sum_{n=1}^{N} \alpha'_n G_{sm_n} G_{m_n d}(T_{sm_n} + T_{m_n d})}{\sum_{n=1}^{N} \alpha'_n G_{sm_n} G_{m_n d}}$$

A configuration m is considered here which corresponds to N fluorophores distributed in the voxels $m_n$, $1 \leq n \leq N$.

$G_{smn}$ (respectively $G_{mnd}$) represent the energy transfer functions between the source and the voxel $m_n$ (respectively the voxel $m_n$ and the detector d). $T^{theo}_{sd}(\alpha1, \ldots \alpha N)$ thus defined, effectively corresponds to an estimation of $T_{sd} - T_s - T_d - \tau$.

It can be seen that $\chi_{2m}^N$ is the difference (or a residual, and more generally a comparison, this comparison possibly also being formed by a ratio) for at least one measurement, between a magnitude formed by the mean measured source-detector time-of-flight (first-order normalized moment of M(t)) preferably but not necessarily reduced by known temporal magnitudes ($T_s$, $T_d$, $\tau$), and this same magnitude modelled using a contribution of all the fluorophores distributed as per configuration m, via coefficients $\alpha'_i$ each of which is assigned to a fluorophore and which represents the fluorescence emission intensity thereof.

The $\alpha'_n$ are obtained by the minimization operation, as is $\chi_{2m}^N$. The latter, also called the criterion of time-of-flight measurement residual, is also small for configurations m corresponding to the real distribution of the N fluorophores in the medium.

Preferably and as is the case in the above formula, the parameter $\chi_{2m}^N$ can be normalized by a statistical magnitude relating to the distribution of $T_{sd}$. This statistical magnitude acts as confidence indicator, as already explained above for $\chi_{2m}$. Here $\sigma^2(T_{sd})$ has been chosen, but another statistical magnitude (for example standard variation or variance) could be chosen to indicate the confidence assigned to a distribution, but as seen previously, normalization with the coefficient $\sigma^2(T_{sd})$ is preferred.

Other basic parameters obtained from other moments of Msd(t) can be formed. However, the defined basic parameters and $\chi_{1m}^N$ and $\chi_{2m}^N$ are particularly pertinent.

From one or more formed basic parameters $\chi_{im}^N$, it is possible to define a combined parameter $P_m^N$, combining said basic parameters $\chi_{im}^N$. By combination, it is recalled that any arithmetic operation is meant whether linear or not, the simplest operations being multiplication, addition or ratios.

According to one preferred embodiment, using the parameters $\chi_{1m}^N$ and $\chi_{2m}^N$ previously obtained, it is possible to form a parameter $P_m^N$ such that $P_m^N = \chi_{1m}^N + \chi_{2m}^N$. This combined coefficient $P_{mN}$ will be minimal when the distribution of the N fluorophores of index m is the closest to reality.

When $P_m^N$ is a combination of the basic parameters $\chi_{1m}^N$ and $\chi_{2m}^N$, a set of coefficients $\alpha_n$ ($1 < n < N$) or $\alpha'_n$ ($1 < n < N$) can be chosen minimizing either $\chi_{1m}^N$, or $\chi_{2m}^N$, or $P_m^N$.

It is then possible to obtain a combined coefficient $P_m^N$ for all or part of the $M^N$ possible distributions of the N fluorophores in the M voxels, a configuration m corresponding to a positioning of the N fluorophores in voxels $m_1 \ldots m_N$. The distributions are then determined whose combined coefficient $P_m^N$ is lower than a limit value $P_m^N{}_{limite}$ determined by the operator. This value $P_m^N{}_{limite}$ may for example be equal to the highest obtained value $P_m^N$ divided by two.

It is also possible to determine a basic parameter $\chi_{4m}^N$, such that:

$$\chi_{4m}^N = \min_{\alpha_1, \ldots \alpha_N} \left[ \sum_{sd} \frac{(M_{sd}^{(0)} - M_{sd,m}^{theo0}(\alpha_1, \ldots \alpha_N))^2}{\sigma^2(M_{sd}^0)} + \sum_{sd} \frac{\left((T_{sd} - T_s - \sigma - T_d) - (T_{sd,m}^{theo}(\alpha_1, \ldots \alpha_N))\right)^2}{\sigma^2(T_{sd})} \right]$$

where:

$$M_{sd,m}^{theo0}(\alpha_1, \ldots \alpha_N) = \sum_{n=1}^{N} \alpha_n G_{sm_n} G_{m_n d}$$

and:

$$T_{sd,m}^{theo}(\alpha_1, \ldots \alpha_N) = \frac{\sum_{n=1}^{N} \alpha_n G_{sm_n} G_{m_n d}(T_{sm_n} + T_{m_n d})}{\sum_{n=1}^{N} \alpha_n G_{sm_n} G_{m_n d}}$$

This again concerns the computing of a basic parameter $\chi^N_{4,m}$, which, for at least one of said temporal distributions $M_{sd}(t)$, combines at least one magnitude (the two magnitudes concerned here are $M^0{}_{sd}$ and $T_{sd}$) obtained from at least one moment of said distribution, and at least one estimation of these magnitudes (these here being $M^{theo0}{}_{sd,m}$ and $T^{theo0}{}_{sd,m}$), these estimations being made by considering that there are N fluorophores, each occupying a voxel of the medium according to a distribution m.

It is possible to determine $P_m{}^N$ from only one basic parameter $\chi_{im}{}^N$, the parameter $P_m{}^N$ even possibly being equal to a basic criterion $\chi_{im}{}^N$. For example, $P_m{}^N$ can be determined so that:

$$P_m{}^N = \chi^N{}_{4m}$$

When N=1, $\chi_{1m}{}^{N=1} = \chi_{1m}$ and $\chi_{2m}{}^{N=1} = \chi_{2m}$ are effectively found, $\chi_{1m}$ and $\chi_{2m}$ being such as defined in the description of the first embodiment.

The invention is advantageously applied to the locating of tumours with respect to the prostate, but can also be applied to other organs, notably testicles, breast, brain, etc.

Therefore by means of the invention it was possible to reconstruct the fluorescence of capillaries buried at 1 cm or 2 cm.

In this example, by taking into account the accuracy of the temporal measurement, it was possible to reject certain aberrant measurements; since the mean times are obtained by the division of M1 by M0, this ratio becomes most imprecise if there is very little signal.

Figure 11A:
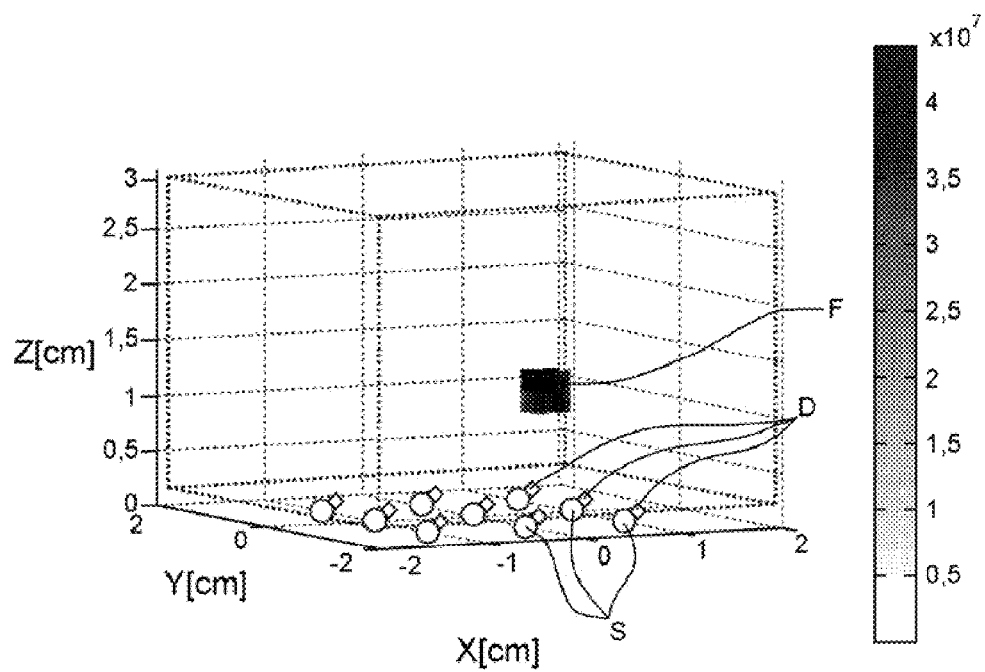
Figure 11B:
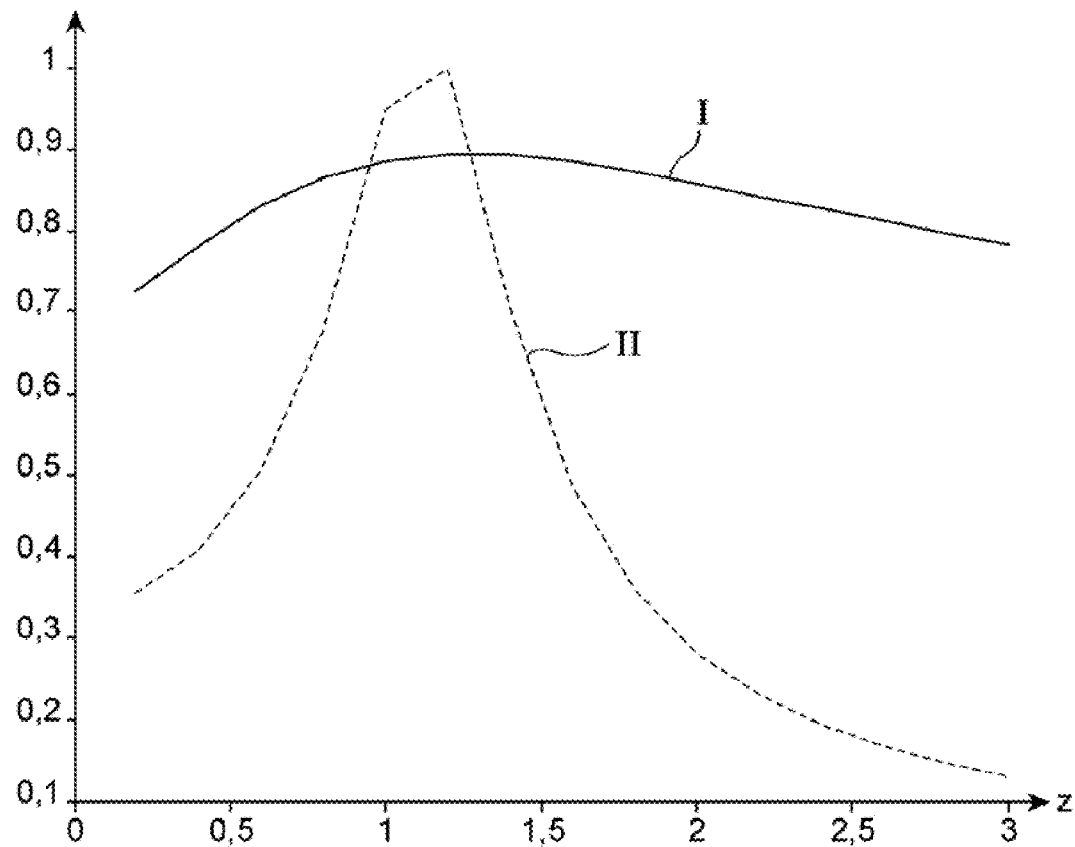

FIGS. 11A-11C et 12A-12C illustrate the results obtained.

FIG. 11A shows a configuration with a capillary at a depth of about 1 cm, with 9 sources S and 9 detectors D arranged in the plane z=0. The value of τ is 0.95 ns. The criterion $\chi_{2m}$ is used here with the approximation $T_s = T_d = 0$. The depth found is z=1.1 cm, for x=0.7 cm and y=0 cm.

The graph in FIG. 11B shows that measurements based on intensities alone (curve I) give imprecise results along z, whilst those based on temporal results give precise results along z (curve II), which confirms FIG. 11C.

FIG. 12A shows a configuration with a capillary at a depth of about 2 cm, with 9 sources S' and 9 detectors D' arranged in the plane z=0. The value of T is 0.95 ns. The criterion $\chi_{2m}$ is used here with the approximation $T_s = T_d = 0$. The depth found is z=1.9 cm, for x=0.2 cm and y=0 cm.

Figure 12B:
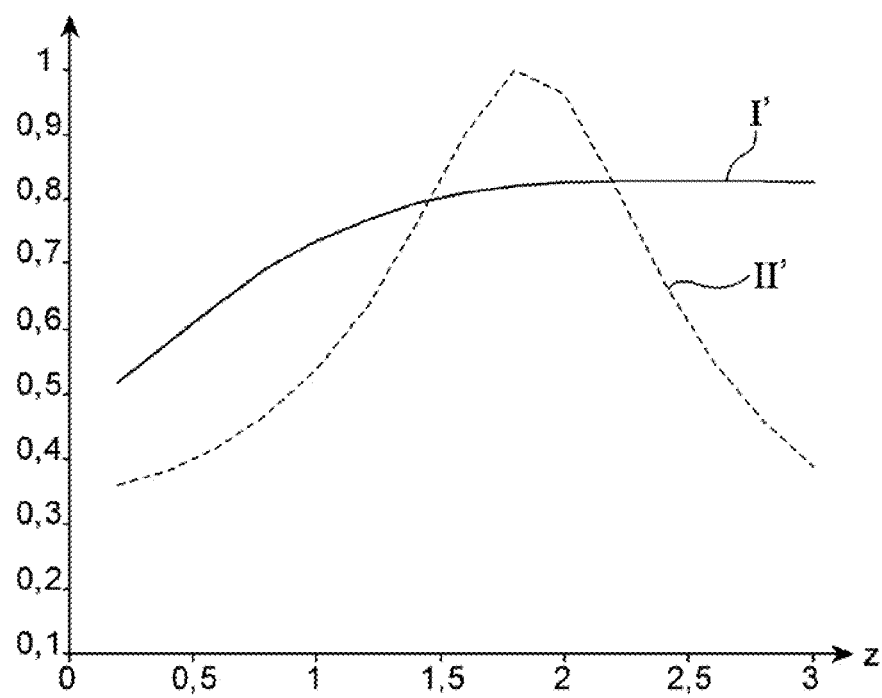
Figure 12C:
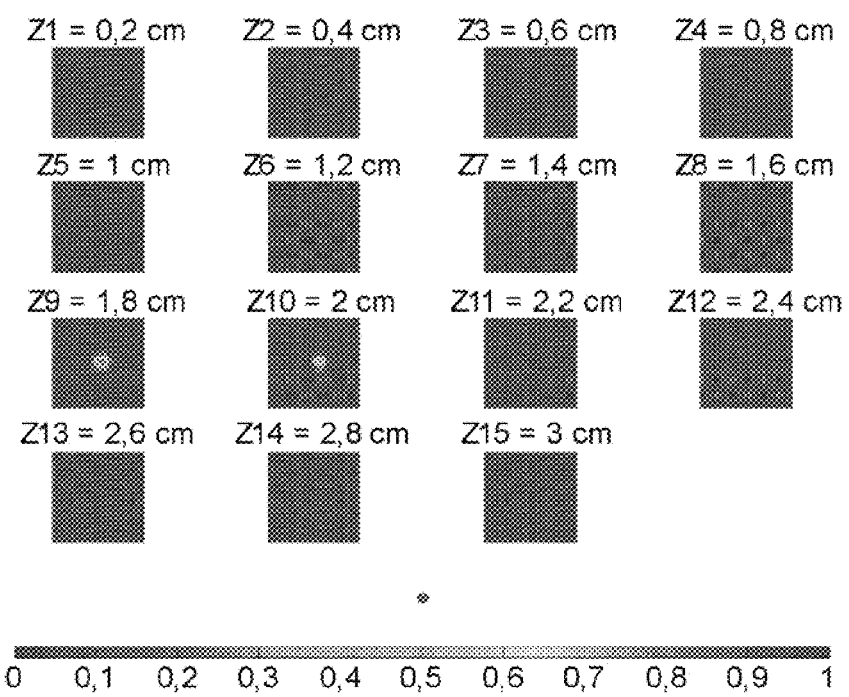

The graph in FIG. 12B shows that measurements based on intensities alone (curve I') give imprecise results along z, whilst those based on temporal results give precise results along z (curve II'), which confirms FIG. 12C.

The invention claimed is:

1. A method for locating at least N (N>1) fluorophores ($F_1$, $F_2$) in a diffusing medium using at least one source ($S_1$-$S_4$, $L_1$-$L_4$) of pulsed radiation capable of emitting radiation to excite this fluorophore, and at least one detector ($D_1$-$D_5$) capable of measuring a fluorescence signal emitted by this fluorophore comprising:
   illumination of the medium by a radiation source,
   detection, by at least one detector, of the signal produced by the medium at the fluorescence wavelength,
   for at least one source-detector pair, performing a temporal distribution $M_{sd}(t)$ of the signal received by the detector,
   the diffusing medium being discretized into M voxels, each fluorophore occupying one voxel among the M voxels of the medium, according to a distribution m,
   the computing of at least one basic parameter $\chi^N{}_{i,m}$, which, for at least one of said temporal distributions $M_{sd}(t)$, combines at least one magnitude obtained from at least one moment of said distribution, and at least one estimation of this magnitude.

2. The method according to claim 1, also comprising the determination of a combined parameter $P_m{}^N$, combining at least one or two basic parameters $\chi^N{}_{i,m}$.

3. The method according to claim 1, one of the basic parameters $\chi^N{}_{2,m}$ comprising:
   a comparison between the first-order normalized moment of said temporal distribution and the modeling of this first-order normalized moment;
   or a comparison between the zero-order moment of said temporal distribution and the modeling of this zero-order moment.

4. The method according to claim 1, comprising the determination of at least one of the following basic parameters:
   the determination of a first basic parameter $\chi^N{}_{1,m}$, which is the sum, for all source-detector pairs, of the differences between the value of the measured intensity $M_{sd}{}^0$ for each source-detector pair and an estimation of the zero-order moment, for each source-detector pair, obtained using the Green functions $G_{smn}$ and $G_{mnd}$, for the source and the detector of each pair, this estimation being made by considering that the N fluorophores are distributed in the voxels of the medium as per configuration m, in which the fluorophores are distributed in the voxels $m_n$;
   the determination of a second basic parameter $\chi^N{}_{2,m}$ which is the sum for all source-detector pairs of the differences, for each source-detector pair, between the mean measured source-detector time-of-flight (first-order normalized moment of M(t)), corrected by known temporal magnitudes relating to the source, to the detector and to the fluorophore, and the estimation of this corrected time-of-flight, this estimation being made by considering that the N fluorophores are distributed in the voxels of the medium as per configuration m.

5. The method according to claim 4, wherein the basic coefficient $\chi 1m^N$ is such that:

$$\chi^N_{1m} = \min_{\alpha_1,\ldots \alpha_N} \sum_{sd} \frac{(M_{sd}^{(0)} - M_{sd,m}^{theo0}(\alpha_1, \ldots \alpha_N))^2}{\sigma^2(M_{sd}^0)}$$

where:

$$M_{sd,m}^{theo0}(\alpha_1, \ldots \alpha_N) = \sum_{n=1}^{N} \alpha_n G_{sm_n} G_{m_n d}$$

a configuration m corresponding to N fluorophores distributed in the voxels $m_n$, $1 \leq n \leq N$, $G_{smn}$ (respectively $G_{mnd}$) representing the energy transfer functions between the source and the voxel $m_n$ (respectively the voxel $m_n$ and the detector d), the coefficients $\alpha_n$, which can be considered as intensities, being obtained by the minimization operation, as is $x_{1m}$;

each element $(M_{sd}{}^0 - M_{sd,m}{}^{theo0}(\alpha_1, \ldots \alpha_N))$ of the sum then representing the difference between:

the value of the measured intensity $M_{sd}{}^0$ for the selected source-detector pair, and an estimation of the zero-order moment $M_{sd}{}^0$, obtained using firstly the Green functions $G_{smn}$ and $G_{mnd}$, and secondly a set of coefficients $\alpha_n$ each of which is assigned to a fluorophore and which represents the fluorescence emission intensity thereof, and the second basic parameter $\chi 2m^N$ being:

$$\chi^N_{2m} = \min_{\alpha'_1,\ldots \alpha'_N} \sum_{sd} \frac{((T_{sd} - T_s - \sigma - T_d) - (T_{sd,m}^{theo}(\alpha'_1, \ldots \alpha'_N)))^2}{\sigma^2(T_{sd})}$$

-continued where:

$$T^{theo}_{sd,m}(\alpha'_1, \ldots \alpha'_N) = \frac{\sum_{n=1}^{N} \alpha'_n G_{sm_n} G_{m_n d}(T_{sm_n} + T_{m_n d})}{\sum_{n=1}^{N} \alpha'_n G_{sm_n} G_{m_n d}}$$

Ts, Td and τ respectively representing the response times of the source, of the detector and the duration of fluorescence of the fluorophore, $Tsm_n$ and $Tm_n d$ representing the respective times-of-flight between the source and the fluorophore located in voxel $m_n$, and between the fluorophore located in voxel $m_n$ and the detector, the coefficient $\sigma^2(Tsd)$ corresponding to an estimation of the distribution variance Tsd, $T^{theo}sd(\alpha'1 \ldots \alpha'N)$ then representing an estimation of the first-order normalized moment of function $M_{sd}(t)$, the coefficients $\alpha'_N$ being obtained by the minimization operation.

6. The method according to claim 1, wherein a combined parameter $P_m^N$, is also determined equal to the sum or product of the basic coefficients $\chi^N_{1,m}$, and $\chi^N_{2,m}$, the combined parameters $P_m^N$ of lowest value then corresponding to the distributions of the fluorophores the closest to the effective distribution of the fluorophores.

7. The method according to claim 1, the number of fluorophores being equal to 1, each basic parameter $\chi^{N=1}_{1,m}$, and $\chi^{N=1}_{2,m}$, then being determined by considering that the fluorophore is single and located in the voxel m.

8. The method according to claim 7, wherein $\chi^{N=1}_{1,m}$, and $\chi^{N=1}_{2,m}$ are determined according to the following equations:

$$\chi_{1m} = \min_{\alpha_m} \sum_{sd} \frac{(M^0_{sd} - \alpha_m \cdot G_{sm} G_{md})^2}{\sigma^2(M^0_{sd})}$$

and $$\chi_{2m} = \sum_{s,d} \frac{((T_{sd} - T_s - \tau - T_d) - (T_{sm} + T_{dm}))^2}{\sigma^2(T_{sd})}$$

$M_{sd}^{(0)}$ representing the zero-order moment of the function Msd(t),

Gsm and Gmd being energy transfer functions, for each source-detector pair sd, between the source s and the voxel m and between the voxel m and the detector d respectively, Tsm and Tdm representing the respective times-of-flight between the source and the voxel m and the voxel m and the detector d, Ts, Td and τ respectively representing the response times of the source, of the detector and the duration of fluorescence of the fluorophore, the coefficient $\sigma^2(Tsd)$ corresponding to an estimation of distribution variance Tsd.

9. The method according to claim 7, wherein a combined parameter $P_m^N$ is also determined equal to the sum or to the product of the basic coefficients $\chi^{N=1}_{1,m}$, and $\chi^{N=1}_{2,m}$, the combined parameters $P_m^{N=1}$ of lowest value then corresponding to the distributions of flurophores the closest to reality.

10. The method according to claim 7, to locate several fluorophores, further comprising at least one of the following steps:

an adjustment step ($S_6$, $S'_9$), to adjust all the intensity contributions of already located fluorophores to the measured intensity;

a computing step ($S_8$, $S'_{11}$) to compute a correlation between the measured intensity and all the intensity contributions of all the fluorophores;

a step ($S'_1$) to increment the number of fluorophores if the computing of a correlation is not satisfactory.

11. The method according to claim 1, wherein the radiation sources and the detectors have reflection geometry.

12. A device for locating at least N (N>1) fluorophores ($F_1$, $F_2$), in a diffusing medium, comprising at least one pulsed radiation source ($S_1$–$S_4$, $L_1$–$L_4$,) capable of emitting radiation to excite this fluorophore and at least one detector ($D_1$–$D_5$) capable of measuring a fluorescence signal emitted by this fluorophore, comprising:

means, for at least one source-detector pair, to perform temporal distribution $M_{sd}(t)$ of the signal received by the detector, means to produce meshing (M) of the volume into mesh elements m or voxels, each of the N fluorophores being distributed in one of the M voxels of the medium as per a distribution m, means to compute at least one basic parameter $\chi^N$,m, which, for at least one of said temporal distributions $M_{sd}(t)$, combines at least one magnitude obtained from at least one moment of said distribution, and at least one estimation of this magnitude.

13. The device according to claim 12, further comprising means to determine a combined parameter $Pm^N$, combining at least one or two basic parameters $\chi^N$i,m.

14. Device according to claim 12, the means to compute at least one parameter comprising means to determine:

a parameter $\chi^N 2$,m comprising the comparison between the first-order normalized moment of said temporal distribution and the modeling of this first-order normalized moment;

or a parameter $\chi^N 1$,m comprising the comparison between the zero-order moment of said temporal distribution and the modeling of this zero-order moment.

15. The device according to claim 12, the means to compute at least one parameter comprising means for:

determining a first basic parameter $\chi^N 1$,m, which is the sum, for all source-detector pairs, of the differences between the value of the measured intensity $M_{sd}^0$ for each source-detector pair, and an estimation of the zero-order moment for each source-detector pair, obtained using the Green functions $G_{smn}$ and $G_{mnd}$, for the source and the detector of each pair, this estimation being made by considering that the N fluorophores are distributed in the voxels of the medium as per configuration m, in which the fluorophores are distributed in the voxels $m_n$;

determining a second basic parameter $\chi^N 2$,m, which is the sum, for all source-detector pairs, of the differences, for each source-detector pair, between the mean measured source-detector time-of-flight (first-order normalized moment of M(t)), corrected by known temporal magnitudes relating to the source, to the detector and to the fluorophore, and the estimation of this corrected time-of-flight, this estimation being made by considering that the N fluorophores are distributed in the voxels of the medium as per configuration m.

16. The device according to claim 15, wherein the basic coefficient $\chi 1m^N$ is such that:

$$\chi_{1m}^{N} = \min_{\alpha_1, \ldots \alpha_N} \sum_{sd} \frac{(M_{sd}^{(0)} - M_{sd}^{theo0}(\alpha_1, \ldots \alpha_N))^2}{\sigma^2(M_{sd}^0)}$$

where:

$$M_{sd}^{theo0}(\alpha_1, \ldots \alpha_N) = \sum_{n=1}^{N} \alpha_n G_{sm_n} G_{m_n d}$$

a configuration m corresponding to N fluorophores distributed in the voxels $m_n$, $1 < n < N$, $G_{smn}$ (respectively $G_{mnd}$) representing the energy transfer functions between the source and the voxel $m_n$ (respectively the voxel $m_n$ and the detector d), the coefficients $\alpha_n$ being obtained by the minimization operation, as is $\Omega 1m$;

each element $(M_{sd}^0 - M_{sd}^{theo0}(\alpha_1, \ldots \alpha_N))$ representing the difference between:

the value of the measured intensity $M_{sd}^0$ for the selected (source-detector) pair, and an estimation of the zero-order moment $M_{sd}^0$, obtained using firstly the Green functions Green $G_{smn}$ and $G_{mnd}$, and secondly a set of coefficients $\alpha_n$ each of which is assigned to a fluorophore and which represents the fluorescence emission intensity thereof, and the second basic parameter $\chi 2m^N$ being such that:

$$\chi_{2m}^{N} = \min_{\alpha'_1, \ldots \alpha'_N} \sum_{sd} \frac{((T_{sd} - T_s - \sigma - T_d) - (T_{sd}^{theo}(\alpha'_1, \ldots \alpha'_N)))^2}{\sigma^2(T_{sd})}$$

where:

$$T_{sd}^{theo}(\alpha'_1, \ldots \alpha'_N) = \frac{\sum_{n=1}^{N} \alpha'_n G_{sm_n} G_{m_n d}(T_{sm_n} + T_{m_n d})}{\sum_{n=1}^{N} \alpha'_n G_{sm_n} G_{m_n d}}$$

Ts, Td and τ respectively representing the response times of the source, of the detector and the duration of fluorescence of the fluorophore, $Tsm_n$ and $Tm_n d$ representing the respective times-of-flight between the source and the fluorophore located in the voxel $m_n$, and between the fluorophore located in the voxel $m_n$ and the detector, the coefficient $\sigma^2(Tsd)$ corresponding to an estimation of distribution variance Tsd, $T^{theo}sd(\alpha'1 \ldots \alpha'N)$ then representing an estimation of the first-order normalized moment of function $M_{sd}(t)$, the coefficients $\alpha_N$ being obtained by the minimization operation.

17. The device according to claim 15, comprising means to determine a combined parameter $P_m^N$, equal to the sum or to the product of the basic coefficients $\chi^N_{1,m}$ and $\chi^N_{2m}$.

18. The device according to claim 12, the number of fluorophores being equal to 1, each basic parameter $\chi^{N=1}_{1,m}$ and $\chi^{N=1}_{2,m}$, then being determined by considering that the fluorophore is single and located in the voxel m.

19. The device according to claim 18, wherein $\chi^{N=1}_{1,m}$ and $\chi^{N=1}_{2,m}$ are determined using the following equations:

$$\chi_{1m} = \min_{\alpha_m} \sum_{sd} \frac{(M_{sd}^0 - \alpha_m \cdot G_{sm} G_{md})^2}{\sigma^2(M_{sd}^0)}$$

and $$\chi_{2m} = \sum_{s,d} \frac{((T_{sd} - T_s - \tau - T_d) - (T_{sm} + T_{dm}))^2}{\sigma^2(T_{sd})}$$

$M_{sd}^0$ representing the zero-order moment of function Msd (t),

Gsm and Gmd being energy transfer functions, for each source-detector pair sd, between the source s and the voxel m and between the voxel m and the detector d respectively, Tsm and Tdm representing the respective times-of-flight between the source and the voxel m and the voxel m and the detector d, Ts, Td and τ respectively representing the response times of the source, of the detector and the duration of fluorescence of the fluorophore, the coefficient $\sigma^2(Tsd)$ corresponding to an estimation of distribution variance Tsd.

20. The device according to claim 12, to locate several fluorophores, further comprising means for cases in which there are several fluorophores to perform at least one of the following steps:

an adjustment step ($S_6$, $S'_9$), to adjust all the intensity contributions of already located fluorophores to the measured intensity;

a computation step of a correlation ($S_8$, $S'_{11}$) between the measured intensity and all intensity contributions of all the fluorophores;

if the number of the several fluorophores is unknown, a step ($S'_1$) to increment the number of fluorophores if the computing of a correlation is not satisfactory.

* * * * *